USO10456541B2

(12) United States Patent
Witt et al.

(10) Patent No.: US 10,456,541 B2
(45) Date of Patent: *Oct. 29, 2019

(54) SYSTEM AND RESPIRATION APPLIANCE FOR SUPPORTING THE AIRWAY OF A SUBJECT

(71) Applicant: KONINKLIJKE PHILIPS N.V., Eindhoven (NL)

(72) Inventors: Erik Kurt Witt, Murrysville, PA (US); William Edwin Clegg, Gibsonia, PA (US); Michael Edward Colbaugh, Level Green, PA (US); Douglas Mechlenburg, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 894 days.

This patent is subject to a terminal disclaimer.

(21) Appl. No.: 14/961,082

(22) Filed: Dec. 7, 2015

(65) Prior Publication Data

US 2016/0082209 A1  Mar. 24, 2016

Related U.S. Application Data

(62) Division of application No. 13/141,782, filed as application No. PCT/IB2009/055629 on Dec. 9, 2009, now Pat. No. 9,216,266.

(51) Int. Cl.
*A61M 16/20* (2006.01)
*A61M 16/00* (2006.01)
*A61M 16/06* (2006.01)

(52) U.S. Cl.
CPC .... *A61M 16/0057* (2013.01); *A61M 16/0666* (2013.01); *A61M 16/20* (2013.01);
(Continued)

(58) Field of Classification Search
CPC .......... A61M 16/0003; A61M 16/0057; A61M 16/0066; A61M 16/022; A61M 16/024;
(Continued)

(56) References Cited

U.S. PATENT DOCUMENTS 5,086,765 A * 2/1992 Levine .................. A61M 15/00
128/200.14
5,148,802 A   9/1992 Sanders
(Continued)

FOREIGN PATENT DOCUMENTS

CN   2546045 A   4/2003
CN   1482934 A   3/2004
(Continued)

OTHER PUBLICATIONS

Hamilton L.H., "Nasal Airway Resistance: Its Measurement and Regulation", 1979, The Physiologist, 22(3)43-49.

*Primary Examiner* — Joseph D. Boecker

(57) ABSTRACT

A respiration appliance, system, and method for supporting the airway of a subject as the subject breaths. The flow of gas from the lungs of the subject during exhalation is leveraged to provide support to the airway. In particular, a body that encloses one or more external orifices of the subject provides a resistance differential between inhaled gas flows and exhaled gas flows that supports the subject's airway.

8 Claims, 8 Drawing Sheets

(52) U.S. Cl.
CPC ......... *A61M 16/205* (2014.02); *A61M 16/024* (2017.08); *A61M 2205/3334* (2013.01); *A61M 2205/50* (2013.01); *A61M 2206/10* (2013.01); *A61M 2230/005* (2013.01); *A61M 2230/40* (2013.01)

(58) Field of Classification Search
CPC .............. A61M 16/06; A61M 16/0666; A61M 16/0672; A61M 16/0677; A61M 16/20; A61M 16/201; A61M 16/202; A61M 16/205; A61M 2205/3334; A61M 2205/50; A61M 2206/10; A61M 2230/005; A61M 2230/40; A61M 2230/42; A61M 2230/46; A61B 5/087
See application file for complete search history.

(56) References Cited

U.S. PATENT DOCUMENTS

| | | | |
|---|---|---|---|
| 5,396,883 A * | 3/1995 | Knupp | A61M 16/20 128/200.14 |
| 5,740,796 A | 4/1998 | Skog | |
| 5,937,855 A | 8/1999 | Zdrojkowski | |
| 6,192,876 B1 * | 2/2001 | Denyer | A61B 5/087 128/204.18 |
| 6,431,171 B1 | 8/2002 | Pavlovburton | |
| 6,478,026 B1 | 11/2002 | Wood | |
| 6,986,353 B2 | 1/2006 | Wright | |
| 7,562,659 B2 | 7/2009 | Matarasso | |
| 8,844,531 B2 * | 9/2014 | Witt | A61M 16/0666 128/204.18 |
| 9,027,553 B2 * | 5/2015 | Witt | A61M 16/0666 128/205.25 |
| 9,216,266 B2 * | 12/2015 | Witt | A61M 16/0666 |
| 9,789,275 B2 * | 10/2017 | Iyer | A61M 16/0666 |
| 2002/0134384 A1 * | 9/2002 | Bienvenu | A61M 15/0086 128/203.29 |
| 2003/0084048 A1 | 5/2003 | Dweck et al. | |
| 2004/0139973 A1 | 7/2004 | Wright | |
| 2005/0133039 A1 | 6/2005 | Wood | |
| 2005/0235992 A1 | 10/2005 | Djupesland | |
| 2005/0252509 A1 * | 11/2005 | Rustad | A61M 16/08 128/203.12 |
| 2005/0284484 A1 | 12/2005 | Curti | |
| 2007/0295338 A1 | 12/2007 | Looms | |
| 2009/0194109 A1 * | 8/2009 | Doshi | A61M 16/0051 128/204.23 |
| 2010/0010362 A1 | 1/2010 | Stasz | |
| 2010/0071693 A1 * | 3/2010 | Allum | A61M 16/04 128/203.27 |
| 2011/0214676 A1 * | 9/2011 | Allum | A61M 16/00 128/207.18 |
| 2016/0082221 A1 * | 3/2016 | Witt | A61M 16/0666 128/204.18 |

FOREIGN PATENT DOCUMENTS

| | | |
|---|---|---|
| CN | 1750854 A | 3/2006 |
| EP | 1402915 A1 | 3/2004 |
| GB | 872634 | 7/1961 |
| JP | 2001523136 A | 11/2001 |
| JP | 20070021215 A | 7/2007 |
| RU | 2072241 C1 | 1/1997 |
| WO | WO9100075 A1 | 1/1991 |
| WO | WO9710869 A1 | 3/1997 |
| WO | WO0234322 A2 | 5/2002 |
| WO | WO2004073778 A1 | 9/2004 |
| WO | WO2004096109 A2 | 11/2004 |
| WO | WO2005011556 A2 | 2/2005 |

\* cited by examiner

SYSTEM AND RESPIRATION APPLIANCE FOR SUPPORTING THE AIRWAY OF A SUBJECT

This patent application is a Divisional of U.S. patent application Ser. No. 13/141,782, filed Jun. 23, 2011, which claims benefit under 35 U.S.C. § 371 of International Application No. PCT/IB2009/055629 filed on Dec. 9, 2009, which claims the priority benefit under 35 U.S.C. § 119(e) of U.S. Provisional Application No. 61/141,252 filed on Dec. 30, 2008, the contents of which are herein incorporated by reference.

This application is related to U.S. Patent Application Ser. No. 61/141,270 filed Dec. 30, 2008, and U.S. Patent Application Ser. No. 61/141,250 filed Dec. 30, 2008, and U.S. Patent Application Ser. No. 61/141,251 filed Dec. 30, 2008, which are hereby incorporated into this application in its entirety.

The invention relates to supporting the airway of a subject as the subject breathes.

Patients that suffer from sleep disordered breathing are typically treated with a Positive Airway Pressure (PAP) device that provides a pressurized flow of breathing gas according to a predetermined mode of ventilation, such as continuous positive airway pressure, proportional positive airway pressure, and proportional assist ventilation, among others. The pressurized gas supports a patient's airway as the patient sleeps such that episodes of cessation of breathing that are associated with sleep disordered breathing are reduced or avoided. PAP devices may be uncomfortable to the patient. This reduces compliance with patients in treatment and may lead to some patients ceasing treatment altogether.

Another treatment for sleep disordered breathing used airway resistors that resist the flow of exhalation from the patient, thereby supporting the airway during exhalation. However, conventional airway resistors are disposed within the airway during treatment, which may be uncomfortable for some patients, and may be somewhat unhygienic. Disposal of conventional airway resistors within, for example, the nostrils of the patient will also reduce the internal cross-sectional area of the nostrils, which may adversely impact the therapy provided by the resistors. Further, airway resistors may be dislodged from the airway of patients, or may implement adhesives (e.g., around the nostrils) to hold the resistors in place. In some cases, conventional airway resistors are considered by some patients to be uncomfortable, and may not provide adequate support for some patients. For example, during inhalation conventional airway resistors may leave the airway completely unsupported, or even reduce the pressure due to some amount of resistance to the flow of inhaled gas.

One aspect of the invention relates to a respiration appliance configured to support the airway of a subject as the subject breathes. In one embodiment, the respiration appliance comprises a body and a set of one or more inhalation valves. The body is configured to enclose one or more external orifices of the airway of a subject. The body forms a plurality of flow paths between the one or more external orifices of the airway of the subject and ambient atmosphere, the plurality of flow paths comprising a first subset of flow paths made up of one or more of but not all of the plurality of flow paths. The set of one or more inhalation valves are disposed in the first subset of flow paths, and permit gas to flow relatively freely from ambient atmosphere to one or more external orifices of the airway of the subject within the first subset of flow paths. The one or more inhalation valves significantly resist or seal the flow of gas from the one or more external orifices of the airway of the subject to ambient atmosphere within the first subset of flow paths. The cumulative resistance to gas flow within the plurality of flow paths formed by the body for gas passing from ambient atmosphere to the one or more external orifices of the airway of the subject is low enough that the subject can inhale freely through the body, and the cumulative resistance to gas flow within the plurality of flow paths formed by the body for gas passing from the one or more external orifices of the airway of the subject to ambient atmosphere is high enough that exhalation by the subject through the body creates a pressure in the airway of the subject that supports the airway during exhalation.

Another aspect of the invention relates to a method of supporting the airway of a subject as the subject breathes. In one embodiment, the method comprises enclosing one or more external orifices of the airway of a subject with a body that forms a plurality of flow paths between the one or more external orifices of the airway and ambient atmosphere, the plurality of flow paths comprising a first subset of flow paths made up of one or more of but not all of the plurality of flow paths; providing, during inhalation, a first cumulative resistance to gas flow within the plurality of flow paths for gas flow through the body from ambient atmosphere to the one or more external orifices of the airway, wherein the first cumulative resistance is low enough that gas is inhaled from ambient atmosphere into the one or more external orifices of the airway substantially unimpeded; and providing, during exhalation, a second cumulative resistance to gas flow within the plurality of flow paths for gas flow through the body from the one or more external orifices of the airway to ambient atmosphere by limiting the flow of gas through a first subset of flow paths without substantially limiting the flow of gas through the other flow paths in the plurality of flow paths formed by the body, wherein the second cumulative resistance is high enough that gas being exhaled through the body elevates pressure within the airway of the subject such that the elevated pressure supports the airway of the subject.

Another aspect of the invention relates to a system configured to support the airway of a subject as the subject breathes. In one embodiment, the system comprises means for enclosing one or more external orifices of the airway of a subject that forms a plurality of flow paths between the one or more external orifices of the airway and ambient atmosphere, the plurality of flow paths comprising a first subset of flow paths made up of one or more of but not all of the plurality of flow paths; means for providing, during inhalation, a first cumulative resistance to gas flow within the plurality of flow paths for gas flow from ambient atmosphere to the one or more external orifices of the airway, wherein the first cumulative resistance is low enough that gas is inhaled from ambient atmosphere into the one or more external orifices of the airway substantially unimpeded; and means for providing, during exhalation, a second cumulative resistance to gas flow within the plurality of flow paths for gas flow from the one or more external orifices of the airway to ambient atmosphere by limiting the flow of gas through a first subset of flow paths without substantially limiting the flow of gas through the other flow paths in the plurality of flow paths formed by the means for enclosing, wherein the second cumulative resistance is high enough that gas being exhaled from the one or more external orifices of the airway of the subject elevates pressure within the airway of the subject such that the elevated pressure supports the airway of the subject.

Another aspect of the invention relates to a respiration appliance configured to support the airway of a subject as the subject breathes. In one embodiment, the respiration appliance comprises a body, one or more valves, and a processor. The body is configured to enclose one or more external orifices of the airway of a subject. The one or more valves are disposed in the body, and are configured to provide a controllable resistance to the flow of gas from the interior of the body to the exterior of the body. The processor is configured to control the resistance of the one or more valves to the flow of gas from the interior of the body to the exterior of the body.

Another aspect of the invention relates to a method of supporting the airway of a subject as the subject breathes. In one embodiment, the method comprises enclosing one or more external orifices of the airway of a subject; and controlling a resistance to gas flow of one or more flow paths through which gas is communicated from the enclosed one or more external orifices of the airway of the subject to ambient atmosphere.

Another aspect of the invention relates to a respiratory appliance configured to support the airway of a subject as the subject breathes. In one embodiment, the respiratory appliance comprises means for enclosing one or more external orifices of the airway of a subject; and means for controlling a resistance to gas flow of one or more flow paths through which gas is communicated from the enclosed one or more external orifices of the airway of the subject to ambient atmosphere.

Another aspect of the invention relates to a system configured to support the airway of a subject as the subject breathes. In one embodiment, the system comprises a respiration appliance, a pressure generator, and a circuit. The respiration appliance is configured to control gas flow between ambient atmosphere and one or more external orifices of the airway of a subject. The respiration appliance has a first resistance to gas flow for gas passing from ambient atmosphere into the airway of the subject past the respiration appliance and a second resistance to gas flow for gas passing from the airway of the subject to ambient atmosphere past the respiration appliance. The first resistance is significantly lower than the second resistance such that during inhalation gas passes from ambient atmosphere into the airway of the subject past the respiration appliance substantially unimpeded and during exhalation the second resistance of the respiration appliance to gas passing from the airway of the subject to ambient atmosphere elevates pressure within the airway of the subject such that the elevated pressure supports the airway of the subject. The pressure generator is configured to generate a pressurized flow of breathable gas. The circuit forms a gas flow path between the respiration appliance and the pressure generator that delivers the pressurized flow of breathable gas from the pressure generator to the airway of the subject via the respiration appliance.

Another aspect of the invention relates to a method of supporting the airway of a subject as the subject breathes. In one embodiment, the method comprises, during inhalation of a subject, providing a first resistance to gas flow for gas passing from ambient atmosphere into one or more external orifices of the airway of the subject; during exhalation of the subject, providing a second resistance to gas flow for gas passing from the one or more external orifices of the airway of the subject to ambient atmosphere, wherein the first resistance is significantly lower than the second resistance such that during inhalation gas passes from ambient atmosphere into the one or more external orifices of the airway of the subject substantially unimpeded and during exhalation the second resistance elevates pressure within the airway of the subject such that the elevated pressure supports the airway of the subject; generating a pressurized flow of breathable gas; and delivering the pressurized flow of breathable gas to the one or more external orifices of the airway of the subject as the subject breathes.

Another aspect of the invention relates to a system configured to support the airway of a subject as the subject breathes. In one embodiment, the system comprises means for, during inhalation of a subject, providing a first resistance to gas flow for gas passing from ambient atmosphere into one or more external orifices of the airway of the subject; means for, during exhalation of the subject, providing a second resistance to gas flow for gas passing from the one or more external orifices of the airway of the subject to ambient atmosphere, wherein the first resistance is significantly lower than the second resistance such that during inhalation gas passes from ambient atmosphere into the one or more external orifices of the airway of the subject substantially unimpeded and during exhalation the second resistance elevates pressure within the airway of the subject such that the elevated pressure supports the airway of the subject; means for generating a pressurized flow of breathable gas; and means for delivering the pressurized flow of breathable gas to the one or more external orifices of the airway of the subject as the subject breathes.

Another aspect of the invention relates to a respiration appliance configured to support the airway of a subject as the subject breathes. In one embodiment, the respiration appliance comprises a body, a set of one or more inhalation valves, and a circuit port. The body is configured to enclose one or more external orifices of the airway of a subject, and forms a plurality of flow paths between the one or more external orifices of the airway of the subject and ambient atmosphere. The plurality of flow paths comprise a first subset of flow paths made up of one or more of but not all of the plurality of flow paths. The set of one or more inhalation valves are disposed in the first subset of flow paths, and permit gas to flow relatively freely from ambient atmosphere to one or more external orifices of the airway of the subject within the first subset of flow paths. The one or more inhalation valves significantly resist or seal the flow of gas from the one or more external orifices of the airway of the subject to ambient atmosphere within the first subset of flow paths. The cumulative resistance to gas flow within the plurality of flow paths formed by the body for gas passing from ambient atmosphere to the one or more external orifices of the airway of the subject is low enough that the subject can inhale freely through the body, and the cumulative resistance to gas flow within the plurality of flow paths formed by the body for gas passing from the one or more external orifices of the airway of the subject to ambient atmosphere is high enough that exhalation by the subject through the body creates a pressure in the airway of the subject that supports the airway during exhalation. The circuit port is formed in the body and is configured to connect the interior of the body with a circuit that delivers a pressurized flow of breathable gas to the body through the circuit port.

Another aspect of the invention relates to a method of supporting the airway of a subject as the subject breathes. In one embodiment, the method comprises, during inhalation of a subject, providing a first resistance to gas flow for gas passing from ambient atmosphere into one or more external orifices of the airway of the subject; during exhalation of the subject, providing a second resistance to gas flow for gas passing from the one or more external orifices of the airway of the subject to ambient atmosphere, wherein the first resistance is significantly lower than the second resistance such that during inhalation gas passes from ambient atmosphere into the one or more external orifices of the airway of the subject substantially unimpeded and during exhalation the second resistance elevates pressure within the airway of the subject such that the elevated pressure supports the airway of the subject; receiving a pressurized flow of breathable gas; and directing the pressurized flow of breathable gas to the one or more external orifices of the airway of the subject as the subject breathes.

Another aspect of the invention relates to a respiration appliance configured to support the airway of a subject as the subject breathes. In one embodiment, the respiration appliance comprises means for, during inhalation of a subject, providing a first resistance to gas flow for gas passing from ambient atmosphere into one or more external orifices of the airway of the subject; means for, during exhalation of the subject, providing a second resistance to gas flow for gas passing from the one or more external orifices of the airway of the subject to ambient atmosphere, wherein the first resistance is significantly lower than the second resistance such that during inhalation gas passes from ambient atmosphere into the one or more external orifices of the airway of the subject substantially unimpeded and during exhalation the second resistance elevates pressure within the airway of the subject such that the elevated pressure supports the airway of the subject; means for receiving a pressurized flow of breathable gas; and means for directing the pressurized flow of breathable gas to the one or more external orifices of the airway of the subject as the subject breathes.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. As used in the specification and in the claims, the singular form of "a", "an", and "the" include plural referents unless the context clearly dictates otherwise.

Figure 1:
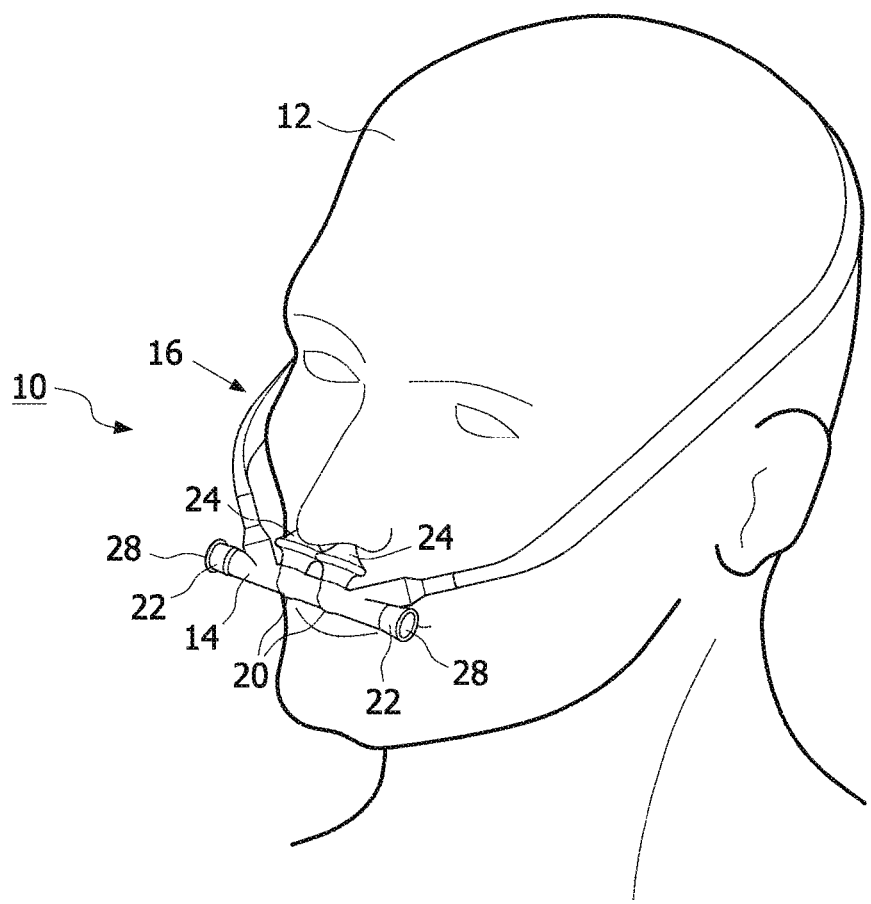
FIG. 1 illustrates a respiration appliance configured to support the airway of a subject, in accordance with one or more embodiments of the invention.

FIG. 1 illustrates a respiration appliance 10 configured to support the airway of a subject 12 as subject 12 breaths, in accordance with one or more embodiments of this disclosure. Respiration appliance 10 leverages the pressurized flow of gas generated by exhalation of subject 12 to pressurize the airway of subject 12 for support purposes. In one embodiment, respiration appliance 10 includes a body 14 that encloses one or more external orifices (e.g., nostrils) of the airway of subject 12 and a fastener 16.

Fastener 16 holds body 14 in place over the one or more external orifices of the airway of subject 12. In the embodiment shown in FIG. 1, fastener 16 is a single strap that loops around the head of subject 12. In one embodiment, fastener 16 includes a headgear having a different configuration for engaging the head of fastener 16 to hold body 14 in place. In one embodiment, fastener 16 includes a structure that engages the interior of the one or more openings of the airway of subject 12, and/or an adhesive that attaches to the skin of subject 12 to hold body 14 in place. In some instances (not shown), respiration appliance 10 may be implemented and/or formed integrally with an oral appliance and/or headgear that holds the lower jaw of subject 12 in a position that opens the airway of subject 12 (e.g., with the lower jaw extended forward), and/or holds the mouth of subject 12 closed to encourage breathing through the nostrils.

Figure 2:
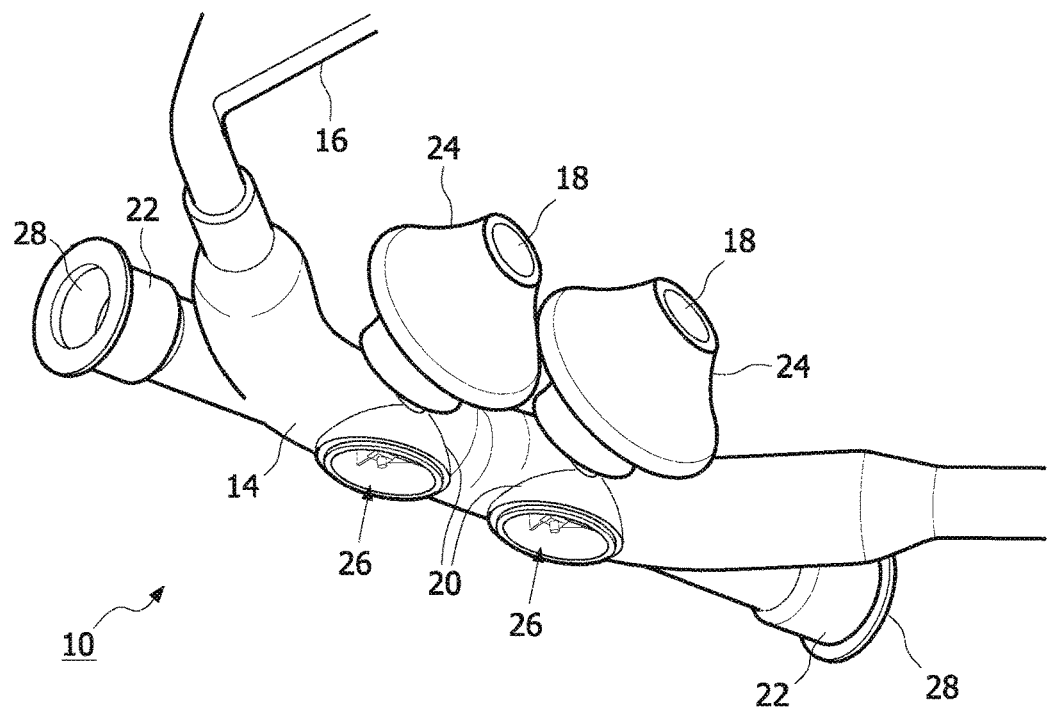
FIG. 2 illustrates a respiration appliance configured to support the airway of a subject, in accordance with one or more embodiments of the invention.

FIG. 2 shows an enlarged view of body 14, according to one or more embodiments of this disclosure. As can be seen in FIG. 2, body 14 forms a plurality of openings with flow paths therebetween. In one embodiment, the interior of body 14 is hollow, and without substantial impediment to the flow of gas from any of the various openings to any of the other various openings. The plurality of openings include one or more subject interface openings 18, a set of inhalation ports 20 and a set of exhalation ports 22. The subject interface openings 18 communicate gas within the flow paths formed inside of body 14 with the airway of subject 12. As will be described further below, body 14 forms a first subset of flow paths between inhalation ports 20 and subject interface openings 18 that deliver gas from ambient atmosphere to the one or more external orifices of the airway of subject 12 during inhalation. Body 14 forms a second subset of flow paths between exhalation ports 22 and subject interface openings 18 that deliver gas from the one or more external orifices of subject 12 to ambient atmosphere during exhalation.

In one embodiment, subject interface openings 18 are formed by airway enclosing members 24. FIG. 2 depicts airway enclosing members 24 as nasal pillows that enclose the nostrils of subject 12. Airway enclosing members 24 may be selectably detachable from the rest of body 14. This will facilitate cleaning and/or replacement of airway enclosing members 24 for hygienic purposes, and/or selection of airway enclosing members 24 by subject 12 based on personal preference (e.g., from members having different sizes, different sized openings, etc.).

At the set of inhalation ports 20, respiration appliance 10 includes a set of inhalation valves 26. Inhalation valves 26 permit gas to flow relatively freely from ambient atmosphere into the flow paths formed within body 14 through inhalation ports 20, but significantly resist or seal the flow of gas from within body 14 to ambient atmosphere through inhalation ports 20. For example, inhalation valves 26 may be "one way" valves that permit gas to flow freely into body 14 from atmosphere, but block gas within body 14 from flowing to atmosphere. As such, during inhalation, the flow paths formed within body between inhalation ports 20 and subject interface openings 18 allow gas to be drawn freely from inhalation ports 20 to subject interface openings 18 and into the nostrils of subject 12. However, during exhalation, inhalation valves 26 significantly resist or seal the flow of exhaled gas from the nostrils of subject 12 to ambient atmosphere through the first subset of flow paths formed within body 14 from subject interface openings 18 to inhalation ports 20. In one embodiment, inhalation valves 26 are selectably detachable from the rest of body 14. This facilitates cleaning of valves 26 and/or body 14, and may enable valves 26 to be replaced for hygienic purposes, or if one of inhalation valves 26 stops functioning correctly.

As used herein, gas flowing "freely" from ambient atmosphere through inhalation ports 20 refers to gas flows that experience a relatively small amount of resistance such that the inhalation of this gas requires approximately the same amount of effort on the part of subject as inhalation without the respiration appliance 10. For example, in one embodiment, the resistance of inhalation valves 26 to gas flowing from ambient atmosphere into body 14 is small enough that the cumulative resistance of respiration appliance 10 to gas inhaled by subject 12 through body 14 is less than or equal to about 0.025 cm $H_2O$/LPM (at 30 LPM flow). In one embodiment, the resistance of inhalation valves 26 to gas flowing from ambient atmosphere into body 14 is small enough that the cumulative resistance of respiration appliance 10 to gas inhaled by subject 12 through body 14 is less than or equal to about 0.017 cm $H_2O$/LPM (at 30 LPM flow). Cumulative resistance is the overall resistance of respiration appliance 10 for a volume of gas flowing into a first set of openings in respiration appliance 10, through respiration appliance 10, and out of respiration appliance via a second set of openings in respiration appliance 10.

At the set of exhalation ports 22, respiration appliance 10 includes a set of exhalation valves 28. Exhalation valves 28 regulate the flow of gas between the nostrils of subject 12 and ambient atmosphere within the second subset of flow paths formed inside body 14 between subject interface openings 18 and exhalation ports 22. In particular, exhalation valves 28 provide a resistance to the flow of gas from the nostrils of subject 12 to ambient atmosphere in the second subset of flow paths during exhalation. The resistance provided by exhalation valves 28 to these flows of exhaled gas are the primary source of a cumulative resistance of respiration appliance 10 to gas being exhaled from the nostrils of subject 12. In fact, if inhalation valves 26 seal inhalation ports 20 against gas flow from within body 14 to ambient atmosphere, then the cumulative resistance of exhalation valves 28 to the flow of gas exhaled through the nostrils of subject 12 to atmosphere is the cumulative resistance of respiration appliance to gas exhaled from the nostrils of subject 12. Exhalation valves 28 are configured such that the cumulative resistance to the flow of exhaled gas to ambient atmosphere through body 14 is high enough that exhalation by subject 12 through body 14 creates a pressure in the airway of subject 12 that supports the airway during exhalation. By way of non-limiting example, the pressure in the airway of subject 12 may be at or above 10 cm $H_2O$ at peak expiration pressure (e.g., at 30 LPM flow). In one embodiment, the pressure created by respiration appliance 10 in the airway of subject 12 may provide at least 1.0 cm $H_2O$ (e.g., at 20 LPM flow).

In one embodiment, exhalation valves 28 have a different resistance to gas flowing from ambient atmosphere to the nostrils of subject 12 through body 14 during inhalation than for gas flowing from the nostrils of subject 12 to ambient atmosphere during exhalation (e.g., exhalation valves 28 may "close" during inhalation). In one embodiment, exhalation valves 28 are fixed resistors, and have the same resistance to gas flow regardless of the direction in which the gas is flowing. In either of these embodiments, the primary inlets to body 14 for gas from ambient atmosphere during inhalation will be gas flowing through inhalation valves 26 at inhalation ports 20. Thus, the cumulative resistance to the flow of inhaled gas from ambient atmosphere to the nostrils of subject 12 through body 14 is low enough by virtue of inhalation ports 20 that subject 12 is able to inhale through body 14 freely.

As was discussed above, during exhalation by subject 12 through body 14, inhalation valves 26 block the flow of gas from body 14 to ambient atmosphere. This blockage may be accomplished by substantially sealing inhalation ports 20 and or by significantly restricting the flow of gas through inhalation ports 20. By way of example, in one embodiment, inhalation valves 26 substantially seal inhalation ports 20 (e.g., provide a resistance to permit less than or equal to about 2.5 LPM (at 5 cm $H_2O$ pressure) of gas to flow out of inhalation ports 20). As another example, in one embodiment, inhalation valves 26 provide a resistance to gas flow out of body 12 during exhalation that is low enough in comparison with the resistance of exhalation valves 28 to the flow of gas from inside body 14 to ambient atmosphere that the resistance of exhalation valves 28 controls the cumulative resistance of body 14 to exhaled gas flowing to ambient atmosphere from the airway of subject 12. For instance, the resistance of inhalation valves 26 to exhaled gas flowing from body 14 to atmosphere may be more than about 5 times larger than the resistance of exhalation valves 28 to exhaled gas flowing from body 14 to atmosphere. In one embodiment, the resistance of inhalation valves 26 to exhaled gas flowing from body 14 to atmosphere may be more than about 2.5 times larger than the resistance of exhalation valves 28 to exhaled gas flowing from body 14 to atmosphere.

In one embodiment, the resistance of exhalation valves 28 to the flow of gas from the nostrils of subject 12 to ambient atmosphere is configurable to adjust the cumulative resistance of respiration appliance 10 to gas flowing through body 14 from subject interface openings 18 to atmosphere during exhalation. To configure the resistance of exhalation valves 28, valves 28 may be associated with one or more controls through which subject 12 or an automated control mechanism can manipulate, or one or more of exhalation valves 28 may include fixed resistance valves that are selectably detachable from exhalation ports 22 for replacement by valves having the desired resistance. In one embodiment, selectable detachment of exhalation valves 28 may facilitate cleaning of appliance 10 and/or replacement of valves that have worn out. The adjustment of resistance of exhalation valve 28 may include an adjustment to a diameter, a cross-sectional size, and/or an area of one or more openings in body 14 associated with exhalation valve 28.

In one embodiment, exhalation ports 22 may be provided with the appropriate cumulative resistance to exhaled gas without the inclusion of separate exhalation valves 28. For example, the openings in body 14 at exhalation ports 22 may be formed having a shape and/or size that resists the flow of exhaled gas at a level that provides the flow paths within body 14 with the appropriate cumulative resistance to exhaled gas. In one embodiment, port 22 may not protrude from body 14 as is illustrated in FIG. 2, but instead may be formed flush with, or more distributed over, the outer surface of body 14.

The provision of inhalation ports 20 to enable free inhalation through body, and exhalation ports 22 to provide a therapeutic resistance during exhalation provides several enhancements over systems in which a single port or set of ports are provided with valves that both enable free inhalation and therapeutic resistance during exhalation through the same flow paths. For example, by implementing separate inhalation ports 20 and exhalation ports 22, respiration appliance 10 can be formed using fixed resistors for exhalation valves 28, which are simpler, more reliable, and less costly (for parts and/or during assembly of the appliances) than the types of valves that must be implemented in appliances where each opening must provide free inhalation and a therapeutic exhalation resistance. Similarly, due to the relative simplicity of the separately formed inhalation valves 26 and exhalation valves 28, the form factor of respiration appliance 10 may be enhanced. For example, valves 26 and 28, and/or appliance 10 in general may be disposed outside of the nostrils of subject 12 (as is shown in the nasal pillow configuration of FIGS. 1 and 2). In embodiments where valves 26 and 28 are formed outside of the nostrils of subject 12, some or all of the valves may have a larger cross-section than the openings of the nostrils, thereby enabling inhalation resistance of the valves 26 to be reduced. Another enhancement provided by the implementation of exhalation valves 28 in separate parts from inhalation valves 26 is that the resistance of exhalation valves 28 can be made configurable (e.g., by replacement) without disturbing the functionality or integrity of inhalation valves 26.

Nasal cycling is a phenomenon known to investigators working in the field of nasal physiology. As stated by Hamilton in The Physiologist (1979 June; 22(3):43-49): "Nasal cycling consists of a reciprocal change in Rn (nasal resistance) between right and left sides, with little or no change in total Rn. It is observed approximately 80% of the time, whether measured in the same individual or in the population, so it is intermittent in nature. When it occurs, it has a cycle duration which varies from ½ to 4 hours, more commonly 2 to 3½ hours." The air paths through the left and right nostrils of subject 12 to atmosphere form a parallel circuit configuration. The net nasal resistance is therefore the inverse of the sum of the inverses of the individual resistances. Conventional airway resistors form individual left and right series circuits when combined with the left and right nasal resistances, respectively. The added resistances added to these separate circuits by the conventional resistors may unbalance nasal cycling. This can cause increased or decreased total nasal resistance during certain periods in the nasal cycle, which can be uncomfortable to the patient, affect therapeutic efficacy, or even cause arousals during sleep.

By contrast, the embodiment of appliance 10 illustrated in FIGS. 1 and 2 (having no internal barrier within body 14 that separates the nostrils of subject 12) does not affect left and right nostril resistances individually. As such, the natural balance of left and right nasal resistances is unaffected because the parallel component of the circuit (inverse of the sum of the inverses) is prior to, and mathematically independent of the added resistance of appliance 10.

Figure 3:
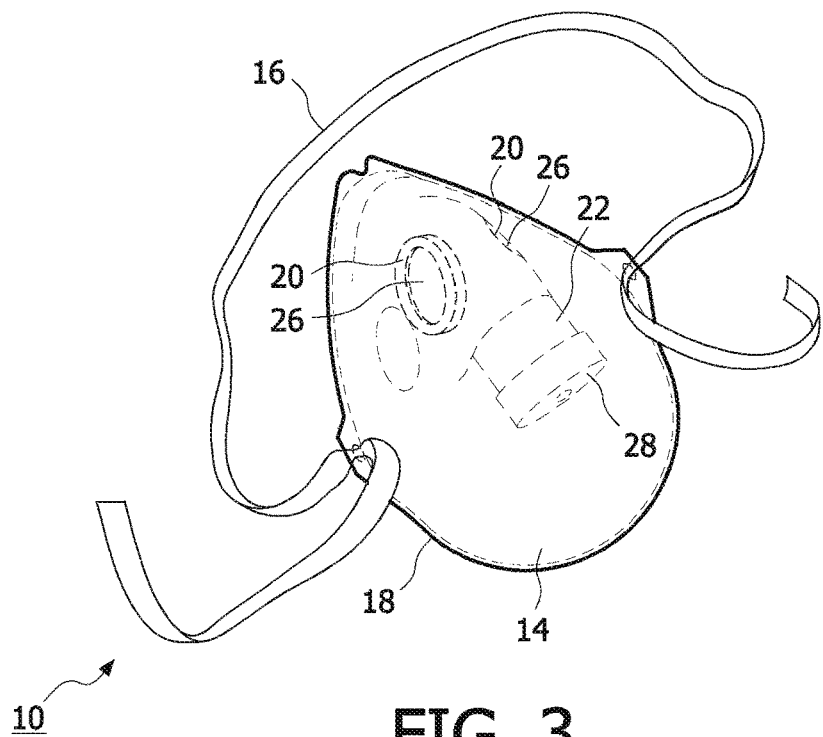
FIG. 3 illustrates a respiration appliance configured to support the airway of a subject, in accordance with one or more embodiments of the invention.

FIG. 3 illustrates an embodiment of respiration appliance 10 in which body 14 is formed as a mask that covers one or more external orifices of the airway of a subject (e.g., the nostrils, the nostrils and mouth, etc.). In the embodiment shown in FIG. 3, body 14 is a membrane surrounding the exterior of the one or more external orifices of the airway of the subject that are being enclosed. Further, the membrane of body 14 forms a plurality of flow paths between one or more external orifices of the airway of the subject and ambient atmosphere. These flow paths include a flow path through body 14 formed by inhalation port 20 and a flow path through body 14 formed by exhalation port 22.

Inhalation valve 26 is disposed within inhalation port 20, and permits gas from atmosphere to be inhaled by the subject through body 14 relatively freely. Exhalation valve 28 is disposed within exhalation port 22, and restricts the flow of gas from within body 14 to atmosphere such that exhalation of gas from the one or more external orifices of the airway of the subject that are enclosed by body 14 cause pressure within the airway of the subject to be elevated to a level that supports the airway of the subject during exhalation. As was described above with respect to the embodiments illustrated in FIGS. 1 and 2, the embodiment of respiration appliance 10 illustrated in FIG. 3 may enable one or both of inhalation valve 26 and/or exhalation valve 28 to be removed from inhalation port 20 or exhalation port 28, respectively. Further, in one embodiment, the resistance to gas flow at exhalation port 22 is configurable by manipulatable control and/or by replacing exhalation valve 26 with another valve having a different resistance. In embodiments in which body 14 covers all airway orifices (e.g., the embodiment shown in FIG. 3), one or both of inhalation ports 20 may be duplicated for back-up purposes.

The formation of body 14 as a mask (e.g., as depicted in FIG. 3), rather than the nasal pillow configuration shown in FIGS. 1 and 2 may be preferred by some subjects due to a perceived comfort, for support provided via additional external orifices (e.g., where the mask covers the mouth as well as the nostrils), and/or for other reasons. It will be apparent that the mechanism of operation of the embodiment of respiration appliance 10 shown in FIG. 3 is identical to the embodiments illustrated in FIGS. 1 and 2 in elevating pressure within the airway of the subject during exhalation. Although further aspects of respiration appliance 10 are described below in terms of embodiments in which respiration appliance 10 implements the nasal pillow configuration of FIGS. 1 and 2, this is not intended to be limiting and these descriptions could be extended by one of ordinary skill in the art to the mask of FIG. 3.

In one embodiment, the mask may be designed to minimize dead-space of the inner volume enclosed against the face. The interface chamber for the nasal orifices may be separated from the oral interface by a pressure barrier or one way valve. Separating the chambers may enhance the pressure sealing structures, and/or may avoid discomfort of re-breathing the extra oral dead-space exhaled gasses when the subject is nose-breathing.

In one embodiment, the portion of body 14 that sits on the bridge of the nose of the subject may be configured to form a secure seal with the skin of the subject. For example, this section of body 14 may include an adhesive (e.g., hydrogel, etc.) to adhere to the subject. In some instances, this section of body may be formed from a relatively springy material that, by virtue of the adhesion between body 14 and the bridge of the nose, holds open the nasal passages of the subject.

Figure 4:
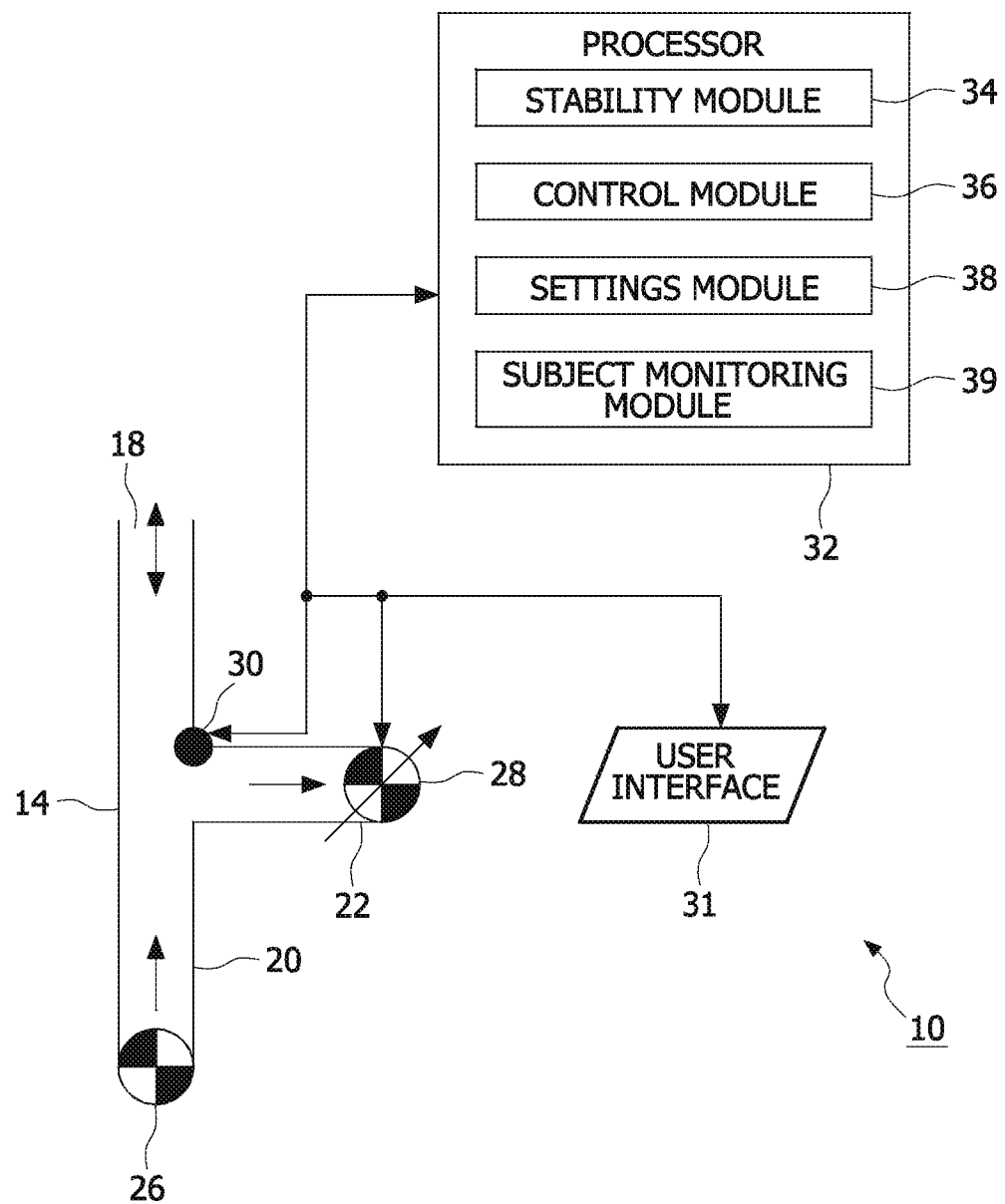
FIG. 4 illustrates a system configured to support the airway of a subject, in accordance with one or more embodiments of the invention.

FIG. 4 is a block diagram of respiration appliance 10 according to one embodiment of this disclosure. In the diagram shown in FIG. 4, in addition to body 14, inhalation port 20, exhalation port 22, inhalation valve 26, and exhalation valve 28, respiration appliance 10 includes one or more sensors 30, a user interface 31, and a processor 32.

Sensor 30 is configured to generate one or more output signals that convey information related to the stability of the airway of the subject on which respiration appliance 10 is installed (e.g., as shown in FIG. 1 and described above). In one embodiment, sensor 30 is carried on body 10. By way of non-limiting example, sensor 30 may monitor one or more parameters of gas at or near the airway of the subject (e.g., within body 14). The one or more parameters may include one or more of flow, pressure, and/or other parameters. In one embodiment, sensor 30 includes a transducer that transduces vibration to an electrical output signal. The output signal generated by the transducer may transduce vibration in sound waves generated by instability in the airway of the subject (e.g., "snoring"), vibration of tissues around the airway of the subject caused by airway instability, and/or other vibrations indicative of airway instability. In one embodiment, sensor 30 is not carried on body 10. For example, sensor 30 may include one or more sensors that monitor the respiratory demand of the subject, the neural activity of the subject, and/or other parameters indicative of the state of the airway of the subject.

User interface 31 is configured to provide an interface between appliance 10 and a user (e.g., the subject, a caregiver, a sleeping companion, etc.) through which the user may provide information to and receive information from appliance 10. This enables data, results, and/or instructions and any other communicable items, collectively referred to as "information," to be communicated between the user and processor 32. Examples of interface devices suitable for inclusion in user interface 31 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as user interface 31. For example, the present invention contemplates that user interface 31 may be integrated with a removable electronic storage interface. In this example, information may be loaded into appliance 10 from removable storage (e.g., a smart card, a flash drive, a removable disk, etc.) that enables the user(s) to customize the implementation of appliance 10. Other exemplary input devices and techniques adapted for use with appliance 10 as user interface 31 include, but are not limited to, an RS-232 port, RF link, an IR link, modem (telephone, cable or other). In short, any technique for communicating information with appliance 10 is contemplated by the present invention as user interface 31.

Processor 32 is configured to provide information processing capabilities in respiration appliance 10. As such, processor 32 may include one or more of a digital processor, an analog processor, a digital circuit designed to process information, an analog circuit designed to process information, a state machine, and/or other mechanisms for electronically processing information. Although processor 32 is shown in FIG. 4 as a single entity, this is for illustrative purposes only. In some implementations, processor 32 may include a plurality of processing units. These processing units may be physically located within the same device, or processor 32 may represent processing functionality of a plurality of devices operating in coordination. In one embodiment, processor 32 is carried by body 14.

As is shown in FIG. 4, in one embodiment, processor 32 includes a stability module 34, a control module 36, a settings module 38, a subject monitoring module 39, and/or other modules. Modules 34, 36, 38, and/or 39 may be implemented in software; hardware; firmware; some combination of software, hardware, and/or firmware; and/or otherwise implemented. It should be appreciated that although modules 34, 36, 38, and 39 are illustrated in FIG. 4 as being co-located within a single processing unit, in implementations in which processor 32 includes multiple processing units, modules 34, 36, 38, and/or 39 may be located remotely from the other modules. Further, the description of the functionality provided by the different modules 34, 36, 38, and/or 39 described below is for illustrative purposes, and is not intended to be limiting, as any of modules 34, 36, and/or 38 may provide more or less functionality than is described. For example, one or more of modules 34, 36, 38, and/or 39 may be eliminated, and some or all of its functionality may be provided by other ones of modules 34, 36, and/or 38. As another example, processor 32 may include one or more additional modules that may perform some or all of the functionality attributed below to one of modules 34, 36, 38, and/or 39.

Stability module 34 is configured to determine the stability of the airway of the subject. The stability of the airway of the subject is determined based on the output signals generated by sensor 30. In one embodiment, the determination of the stability of the airway of the subject made by stability module 34 includes identifications of instances of instability in the airway of the subject above a predetermined threshold. In one embodiment, the determination of the stability of the airway of the subject made by stability module 34 includes a measurement of the stability of the airway of the subject.

In the embodiment of respiration appliance 10 illustrated in FIG. 4, exhalation valve 28 is configured to provide a controllable resistance to the flow of gas from the interior of body 14 to ambient atmosphere (e.g., exhaled gas). Control module 36 is configured to control the resistance of exhalation valve 28 to this flow of gas. More particularly, control module 36 controls the resistance of exhalation valve 28 to the flow of gas from the interior of body 14 to ambient atmosphere based on the determinations of airway stability made by stability module 34. For example, if stability module 34 determines that the airway of the subject is open and stable, the resistance of exhalation valve 28 to the flow of gas from the interior of body 14 to ambient atmosphere is controlled by control module 36 to be relatively small, thereby permitting the subject to exhale freely through body 14. If, on the other hand, stability module determines that the airway of the subject has become unstable, the resistance of exhalation valve 28 to gas flowing from the interior of body 14 to ambient atmosphere is increased to increase pressure within the airway of the subject during exhalation, thereby stabilizing the airway of the subject. This control of exhalation valve 28 may enhance the comfort of respiration appliance 10 to the subject, particularly at times when the airway of the subject is stable.

In one embodiment, control module 36 controls the resistance of exhalation valve 20 to the flow of gas from the interior of body 14 to ambient atmosphere in accordance with an algorithm that is designed to enhance the comfort of subject 12. For example, control module 36 may set the resistance of exhalation valve 20 at a relatively low initial value, and then ramp the resistance up over time to a therapeutic value. This may enable the subject to become accustomed to the pressurization of the airway gradually over time. In some cases, this may enable the subject to fall asleep at a relatively low resistance, and then to receive therapeutic support at the therapeutic value for resistance after falling asleep. In one embodiment, control module 36 may enable the subject to reset the resistance value back to the initial resistance (e.g., via a user interface). This may enable the subject to reduce the resistance of exhalation valve 20 upon waking, thereby enhancing the comfort of the subject so that the subject can fall asleep again.

Settings module 38 is configured to enable the subject to configure, at least somewhat, the manner in which control module 36 responds to decreases in the stability of the airway. For example, settings module 38 may enable the subject to set a sensitivity of control module 36 to airway instability, an amount of increase to be applied to the resistance of exhalation valve 28 to exhaled gas upon detection of airway instability, and/or configure other parameters of respiration appliance 10 controlled by control module 36. In one embodiment, settings module 38 is accessible to the subject via a user interface. The user interface may be carried on body 14, or may include a communication port through which the subject connects respiration appliance with another processing entity (e.g., a computer, a mobile phone, a personal digital assistant, etc.) for configuration of settings module 38. In some instances, valve 28 may be configured such that upon disconnection from processor 32, valve 28 returns to an open or maximum resistance setting.

Subject monitoring module 39 is configured to monitor the subject receiving treatment from appliance 10. In particular, subject monitoring module 39 monitors the state of the condition or syndrome of the subject that causes airway obstructions during sleep. For example, Obstructure Sleep Apnea syndrome ("OSA") tends to be a degenerative condition. Subject monitoring module 39 may monitor the subject in order to provide information to the subject or another user regarding the state of advancement of the OSA suffered by the subject. In some instances, subject monitoring module may monitor one or more of a number of obstructive events (e.g., as identified by stability module 34) one or more parameters of the flow of gas through appliance 10 (e.g., based on output signals generated by sensors 30), and/or other information related to the advancement of OSA, or another condition, suffered by the subject. Subject monitoring module 39 provides an indicator to the subject of the state of the OSA or other condition suffered by the subject via user interface 31.

In one embodiment, subject monitoring module 39 provides an indication to the user on a nightly, weekly, monthly, or other periodic basis of the number of obstructive events suffered by the subject. For instance, if the number of obstructive events breaches a predetermined threshold, an indicator may be provided to the user that the subject may require additional airway support than is currently being provided by appliance 10.

In one embodiment, subject monitoring module 39 provides data procured from sensors 30 and/or stability module 34 to the user via user interface 31. The user may then implement that data to make determinations about the advancement of the OSA or other condition suffered by the subject. In some instances, the data received from subject monitoring module 39 may be used, for example, to perform a phenotyping that classifies the OSA or other condition suffered by the subject, the symptoms of the subject, and/or the physiological causes of the obstructed breathing suffered by the subject.

It will be appreciated that at least some of the features and functionality attributed to respiration appliance 10 in FIG. 4 may be implemented in an embodiment not including an electronic processor such as processor 32. By way of non-limiting example, the gradual ramping of resistance described above with respect to 28 could be accomplished by a mechanical mechanism for gradually restricting gas flow through valve 28 (e.g., by gradually restricting the diameter and/or cross-section of one or more openings formed at valve 28). For instance, a memory polymer may be inserted in one or more openings formed at valve 28. The memory polymer may contract after being enlarged (e.g., by an inserted plug). Valve 28 may include a memory metal/polymer/nano-structure that pulls or pushes a membrane (or membranes) to close an opening associated with valve 28 after the membrane/memory structure is placed in an initial open position by a reset mechanism. Valve 28 may include a spring-based clock-like mechanism that is released by breath pressure pressing against a membrane (or membranes) to slowly close an opening at valve 28. Valve 28 may include a rocking-ratchet clock mechanism (fixed or pre-programmed time actuated) to slowly close a valve opening. Other mechanisms for slowly closing a valve opening associated with valve 28 to ramp resistance are also contemplated.

In one embodiment, the mechanical mechanism included in valve 28 to slowly ramp resistance over time without control from an electrical processor may include an activation control. The activation control may be activated by subject 12, or by another individual in the vicinity of subject 12 during sleep (e.g., a spouse, a parent, a caregiver, etc.) as needed.

As another example, of the types of functionality accomplished in the embodiment of appliance 10 illustrated in FIG. 4 without control by an electronic processor, respiration appliance 10 may include a mechanical mechanism for triggering a change in resistance of valve 28. For example, valve 28 may include a resonant sound chamber and/or tuning fork that is caused to vibrate by snoring of the subject. The resonant sound chamber or tuning fork may be coupled to a clock mechanism or release mechanism that causes one or more openings associated with valve 28 to be restricted.

Figure 5:
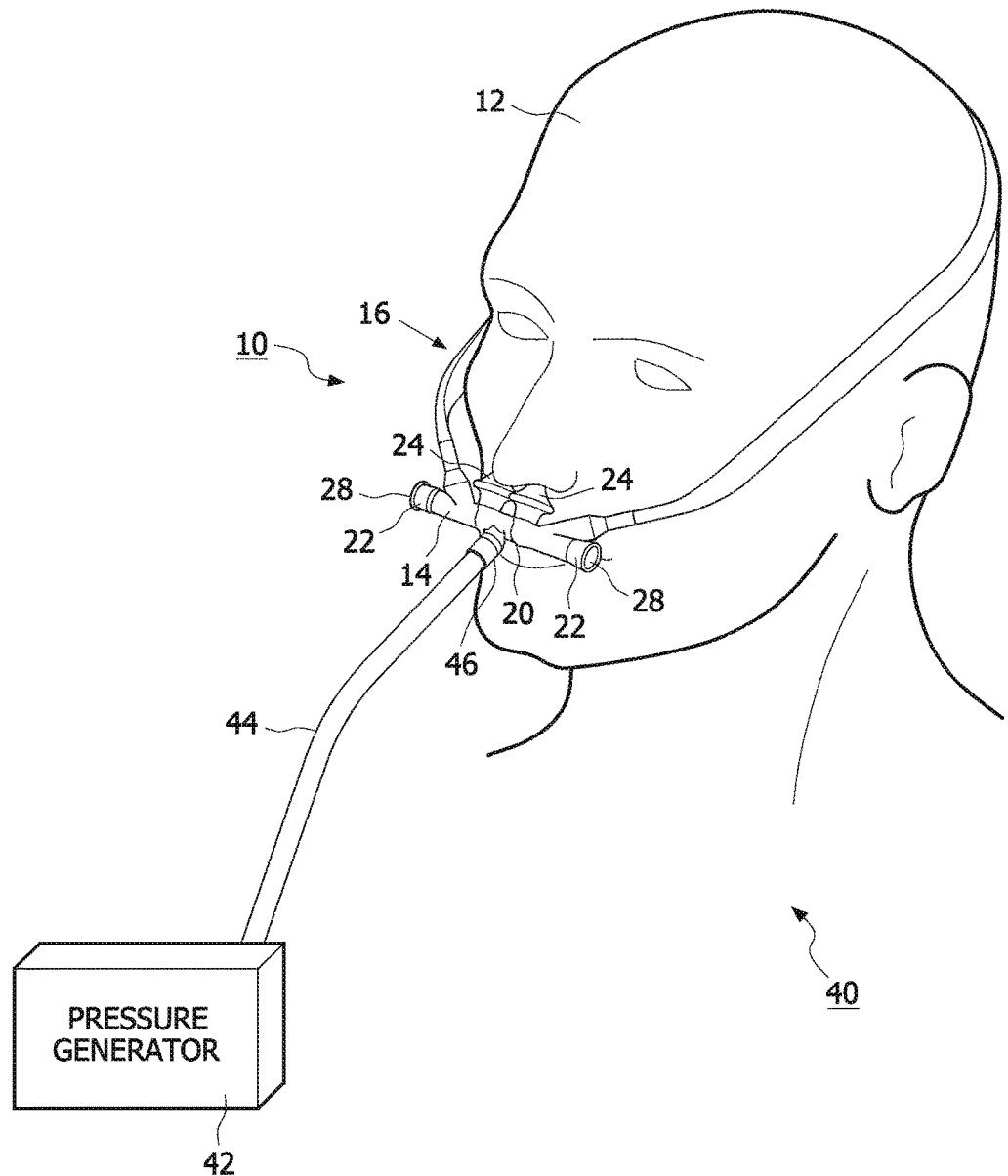
FIG. 5 illustrates a system configured to support the airway of a subject, in accordance with one or more embodiments of the invention.

FIG. 5 illustrates an embodiment of respiration appliance 10 including additional features that enhance the support to the airway of a subject provided by respiration appliance 10. In the embodiment shown in FIG. 5, respiration appliance 10 is implemented as a component in a system 40 configured to support the airway of the subject. In one embodiment, in addition to respiration appliance 10, system 40 includes a pressure generator 42 and a circuit 44.

Pressure generator 42 is configured to generate a pressurized flow of breathable gas for delivery to the airway of the subject via respiration appliance 10. One or more parameters of the pressurized flow of breathable gas generated by pressure generator 42 may be controlled by pressure generator 42 for therapeutic purposes. For example, pressure generator 42 may control one or more of the pressure, the flow rate, the composition, and/or other parameters of the pressurized flow of breathable gas. In one embodiment, pressure generator 42 includes a gas source and a one or more components that control the flow and/or pressure of a pressurized flow of gas generated from the gas within the gas source. The gas source may include may include any supply (or supplies) of breathing gas, such as, for example, ambient atmosphere, a tank of pressurized gas, a wall gas source, and/or other bodies of breathable gas. The breathing gas from the gas source can be any breathable gas, such as air, oxygen, an oxygen mixture, a mixture of a breathing gas and a medication, which can be in gaseous form (e.g., nitric oxide, nebulized, etc.), and/or other breathable gases. The one or more components that control one or more parameters of the pressurized flow of breathable gas may include one or more of a valve, a blower, a piston, a bellows, and/or other mechanisms for controlling one or more parameters of the pressurized flow of breathable gas.

Circuit 44 forms a gas flow path between respiration appliance 10 and pressure generator 42. The gas flow path formed by circuit 44 delivers the pressurized flow of breathable gas generated by pressure generator 42 from pressure generator 42 to respiration appliance 10. In the embodiment shown in FIG. 5, circuit 44 includes a conduit that runs between pressure generator 42 and respiration appliance 10. The conduit is flexible and substantially seals the flow path between pressure generator 42 and respiration appliance 10 from atmosphere. As is discussed below, the flow of pressurized breathable gas is provided to respiration appliance 10 at a relatively low flow rate. As such, the cross-sectional area of circuit 44 may be relatively small. For example, in one embodiment, the cross-sectional area of circuit 44 is less than about 1 $cm^2$. In one embodiment, the cross-sectional area of circuit 44 is less than about 1.5 $cm^2$. In one embodiment, due to the low flow rate of the pressurized flow of breathable gas, circuit 44 is relatively flexible. One or both of the relatively small cross-sectional size of circuit 44 and/or the relative flexibility of circuit 44 may enhance the usability of system with respect to pressure support systems (e.g. conventional PAP systems) that rely on larger flow rates and require bulkier and/or stiffer circuits for delivery. For example, the smaller and/or more flexible circuit 44 may be more comfortable for the subject. As another example, the smaller more flexible circuit 44 may reduce pulling force and/or torque that is translated to respiration appliance 10 during use. This reduction in pulling force and/or torque may enable reductions in size and/or or mass for respiration appliance 10 and/or the apparatus (e.g., the headgear) that holds respiration appliance 10 in place, thereby enabling smaller, less intrusive designs for respiration appliance 10.

In order to receive the pressurized flow of breathable gas from circuit 44, in the embodiment shown in FIG. 5, body 14 of respiration appliance 10 forms a circuit port 46 at which the flow path formed by circuit 44 is communicated with the interior of body 14. In one embodiment, a circuit valve (not shown) is disposed in circuit port 46. The circuit valve controls the flow rate of the pressurized flow of breathable gas into body 14. In some instances, the resistance of the circuit valve is controllably adjustable to enable adjustment of the flow rate of the pressurized flow of breathable gas into body 14. In one embodiment the flow rate of the pressurized flow of breathable is controlled by adjusting the operation of pressure generator 42. In one embodiment, the circuit valve may be designed to control or stop airflow down circuit 44 during exhalation.

In one embodiment, circuit 44 is removable from circuit port 46 and respiration appliance 10 includes a plug (not shown) that can be removably inserted in circuit port 46 to seal circuit port 46 while circuit 44 is removed. In one embodiment, rather than receiving a plug, the circuit valve disposed within circuit port 46 can be closed to prevent gas from ambient atmosphere from entering body 14 through circuit port 46. The sealing of circuit port 46 from ambient atmosphere enables respiration appliance 10 to function as described above (e.g., with respect to FIGS. 1-4) in the absence of circuit 44 being installed in circuit port 46. For example, the subject may want to receive the airway support provided by respiration appliance 10 without the additional support provided by the pressurized flow of breathable gas delivered through circuit 44. As another example, the subject may use respiration appliance 10 without circuit 44 and pressure generator 42 when the subject is away from home and does not want to transport pressure generator 42 and/or circuit 44.

In one embodiment, the pressurized flow of breathable gas is generated by pressure generator 42 at a relatively constant flow rate to provide additional support to the airway of the subject. As has been described above, during respiration, the subject inhales freely from atmosphere through body 14 via flow paths formed between inhalation ports 20 and subject interface openings 18. During exhalation, inhalation ports 20 are closed by inhalation valves 26, and gas exhaled through subject interface openings 18 are exhausted to atmosphere via flow paths between subject interface openings 18 and exhalation ports 22. Due to the resistance of exhalation valves 28 installed in exhalation ports 22, the exhaled gas creates a pressure within the airway of the subject that provides airway support.

As should be appreciated from the foregoing, while respiration appliance without circuit 44 and pressure generator 42 provides support to the airway of the subject during exhalation, the airway is still left relatively unsupported during inhalation. Further, the pressurization of the airway during exhalation is limited by the volume of air exhaled by the subject and/or the size and shape of the airway of the subject. As such, while the use of respiration appliance 10 without pressure generator 42 and circuit 44 may provide an enhanced comfort to the subject over conventional PAP support systems, the support provided by respiration appliance 10 alone during respiration may not be enough to adequately support the subject.

In instances in which the use of respiration appliance 10 alone does not provide the subject with adequate support to the airway, the use of respiration appliance 10 along with pressure generator 42 and circuit 44 provides an intermediate treatment option between the use of respiration appliance 10 alone and a conventional PAP support system. In combination with pressure generator 42 and circuit 44, respiration appliance 10 functions as described above to enable the subject to inhale and exhale to and from atmosphere while providing a level of support to the airway of the subject. The flow rate of the pressurized flow of breathable gas delivered to respiration appliance 10 via circuit 44 is only large enough to maintain airway pressure to an acceptable minimum level during inhalation. As the pressurized flow of gas is neither the primary source of breathable gas delivered to the airway of the subject by respiration appliance 10, nor the primary source of airway support (as is the case in a conventional PAP system), the flow rate of the pressurized flow of breathable gas may be relatively low. For example, in one embodiment, the flow rate of the pressurized flow of breathable gas remainsless than about 100 LPM. In one embodiment, the flow rate of the pressurized flow of breathable gas stays below about 75 LPM. In one embodiment, the flow rate of the pressurized flow of breathable gas stays below about 50 LPM. In one embodiment, the flow rate of the pressurized flow of breathable gas stays below about 40 LPM. The relatively low flow rate of the pressurized gas may provide an enhanced usability (e.g., comfort) to the subject with respect to systems (e.g., conventional PAP systems) that require higher flow rates.

In one embodiment, the flow rate of the pressurized flow of breathable gas is a relatively static parameter that is provided consistently during use. The flow rate for the subject may be determined specifically for the subject. For example, in one embodiment, during a sleep-study, one or more caregivers may determine the appropriate flow rate for the subject. In one embodiment, the appropriate flow rate for the subject is determined by monitoring pressure within the airway of the subject. The appropriate flow rate for the subject is the flow rate that ensures the pressure within the airway of the subject at a transition between exhalation and inhalation does not typically go below a minimum transition airway pressure. The minimum transition airway pressure may be, for example, about 4 cm $H_2O$.

In one embodiment, the flow rate and/or pressure of the pressurized flow of breathable gas from circuit 44 is slowly incremented over time. The incremental increase of the flow rate and/or pressure of the breathable gas from circuit 44 may be incremented from an initial level that may be more comfortable for the subject than the level required for effective therapy during sleep. Over time, the level of flow rate and/or pressure may be incremented to a level that provides effective therapy. This approach may enable the subject to adjust to the reception of therapy via respiration appliance 10 slowly as the pressure and/or flow rate of the breathable gas is incremented. In some instances, the subject may even fall asleep before the increased level of pressure and/or flow rate is achieved. In this embodiment, a control may be provided to the subject to "reset" the flow rate and/or pressure to the initial reduced level. For example, if the subject awakens at night this reset may enable the subject to reduce the level pressure and/or flow rate of the breathable gas while the subject attempts to fall back asleep.

In other embodiments, the pressure and/or flow rate of the breathable gas from circuit 44 is otherwise varied to improve the comfort and/or efficacy of the airway support provided. For example, the pressure and/or flow rate may be varied according in a bi-level mode between a first level during inhalation and a second level during exhalation. As another example, the pressure and/or flow may be increased according to more sophisticated ramping modes than the simple incrementation set forth above, In one embodiment, various parameters of the flow of breathable gas may be controlled in order to provide therapeutic benefits other than simple airway support. For example, a composition of the flow of breathable gas may be controlled (e.g., for supplying supplemental oxygen to the subject), the pressure and/or flow rate of the flow of breathable gas may be controlled to entrain the breathing patterns of the subject (e.g., to reduce breathing rate, increase breath volume, etc.), and/or parameters may be controlled for other therapeutic purposes.

Figure 6:
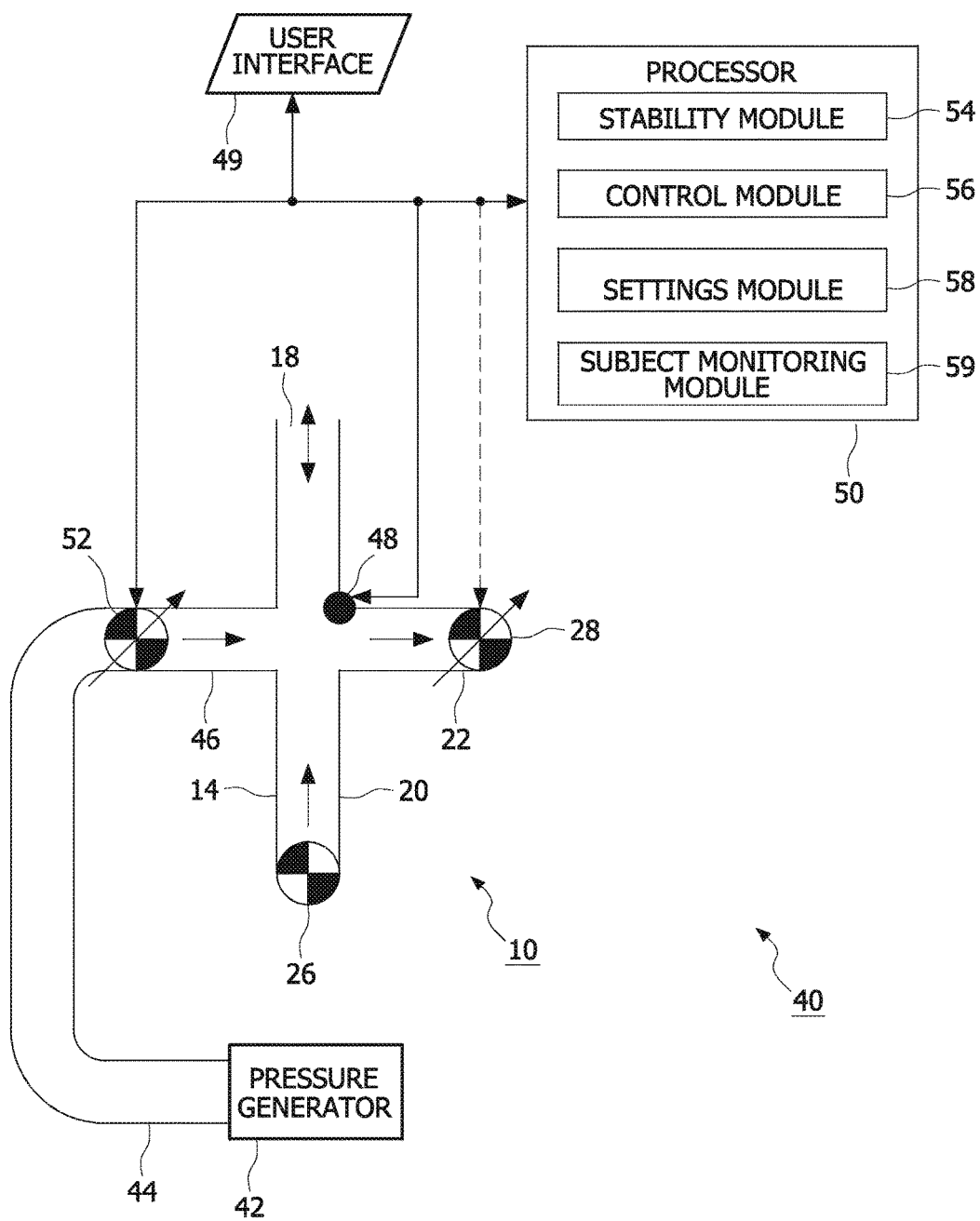
FIG. 6 illustrates a system configured to support the airway of a subject, in accordance with one or more embodiments of the invention.

FIG. 6 is a block diagram of system 40 according to one embodiment of this disclosure. In the diagram shown in FIG. 6, in addition to respiration appliance 10, pressure generator 42, and circuit 44, as discussed above, system 40 includes one or more sensors 48, a user interface 49, and a processor 50. In the embodiment illustrated in FIG. 6, a circuit valve 52 is disposed within circuit port 46 to control the flow rate of the pressurized flow of breathable gas that enters body 14 from circuit 44. It should be appreciated that in one embodiment (not shown), the flow rate of the pressurized flow of breathable gas may be adjusted through control of pressure generator 42, rather than or in addition to the flow rate control provided by circuit valve 52 discussed below.

Sensor 48 is configured to generate one or more output signals that convey information related to the stability of the airway of the subject on which respiration appliance 10 is installed (e.g., as shown in FIG. 1 and described above). In one embodiment, sensor 48 is carried on body 10. In one embodiment, sensor 48 is carried by circuit 44. By way of non-limiting example, sensor 48 may monitor one or more parameters of gas at or near the airway of the subject (e.g., within body 14). The one or more parameters may include one or more of flow, pressure, and/or other parameters. In one embodiment, sensor 48 includes a transducer that transduces vibration to an electrical output signal. The output signal generated by the transducer may transduce vibration in sound waves generated by instability in the airway of the subject (e.g., "snoring"), vibration of tissues around the airway of the subject caused by airway instability, and/or other vibrations indicative of airway instability.

User interface 49 is configured to provide an interface between system 40 and a user (e.g., the subject, a caregiver, a sleeping companion, etc.) through which the user may provide information to and receive information from system 40. User interface 49 may function in substantially the same manner as user interface 31 (shown in FIG. 4 and described above). In one embodiment, user interface 49 includes more than one actual interface. In one embodiment, user interface 49 includes an interface associated with pressure generator 49 and/or an interface associated with appliance 10.

Processor 50 is configured to provide information processing capabilities in system 40. As such, processor 50 may include one or more of a digital processor, an analog processor, a digital circuit designed to process information, an analog circuit designed to process information, a state machine, and/or other mechanisms for electronically processing information. Although processor 50 is shown in FIG. 6 as a single entity, this is for illustrative purposes only. In some implementations, processor 50 may include a plurality of processing units. These processing units may be physically located within the same device, or processor 50 may represent processing functionality of a plurality of devices operating in coordination. In one embodiment, processor 50 is carried by body 14. In one embodiment, processor 50 is carried by circuit 44 and/or pressure generator 42.

As is shown in FIG. 6, in one embodiment, processor 50 includes a stability module 54, a control module 56, a settings module 58, a subject monitoring module 59, and/or other modules. Modules 54, 56, 58, and/or 59 may be implemented in software; hardware; firmware; some combination of software, hardware, and/or firmware; and/or otherwise implemented. It should be appreciated that although modules 54, 56, 58, and 59 are illustrated in FIG. 6 as being co-located within a single processing unit, in implementations in which processor 50 includes multiple processing units, modules 54, 56, 58, and/or 59 may be located remotely from the other modules. Further, the description of the functionality provided by the different modules 54, 56, 58, and/or 59 described below is for illustrative purposes, and is not intended to be limiting, as any of modules 54, 56, 58, and/or 59 may provide more or less functionality than is described. For example, one or more of modules 54, 56, 58, and/or 59 may be eliminated, and some or all of its functionality may be provided by other ones of modules 54, 56, 58, and/or 59. As another example, processor 50 may include one or more additional modules that may perform some or all of the functionality attributed below to one of modules 54, 56, 58, and/or 59.

Stability module 54 is configured to determine the stability of the airway of the subject. The stability of the airway of the subject is determined based on the output signals generated by sensor 48. In one embodiment, the determination of the stability of the airway of the subject made by stability module 54 includes identifications of instances of instability in the airway of the subject above a predetermined threshold. In one embodiment, the determination of the stability of the airway of the subject made by stability module 54 includes a measurement of the stability of the airway of the subject.

In the embodiment of system 40 illustrated in FIG. 6, control module 56 is configured to control the resistance of circuit valve 52 to the flow of pressurized gas from circuit 44 into body 14. By controlling this resistance of circuit valve 52, control module 56 controls the flow rate of the pressurized flow of breathable gas from circuit 44 into body 14. In one embodiment, control module 56 controls the resistance of circuit valve 52 based on the determinations of airway stability made by stability module 54. For example, if stability module 54 determines that the airway of the subject is open and stable, the resistance of circuit valve 52 to the flow of pressurized gas from circuit 44 to body 14 is controlled by control module 56 to be relatively large, thereby reducing or stopping the flow of pressurized gas from circuit 44 to body. If, on the other hand, stability module 54 determines that the airway of the subject has become unstable, the resistance of circuit valve 52 is decreased to permit pressurized gas to flow from circuit 44 to the airway of the subject through body 14, thereby increasing pressure within the airway of the subject to stabilize the airway of the subject during inhalation. This control of circuit valve 52 may enhance the comfort of system 40 to the subject, particularly at times when the airway of the subject is stable. Valve 52 can be positioned anywhere within the pressurized gas circuit, including within the pressure source. Other configurations include a configuration where valve 52 is a shunt to atmosphere. A similar effect could be obtained without valve 52, but controlling blower speed, for example. There are many possible pressure control configurations that should be obvious to those skilled in the art.

In one embodiment, control module 56 increases and/or decreases the resistance of circuit valve 52 incrementally. These incremental increases and/or decreases may be in response to incremental increases and/or decreases in the stability of the airway of the subject, as determined by stability module 54. In one embodiment, control module 56 adjusts the resistance of circuit valve 52 between two resistances that correspond to an open position at which gas is permitted to flow into body 14 from circuit 14 at a predetermined flow rate and a closed position at which the flow of gas from circuit 44 is stopped or significantly slowed. In one embodiment, in response to a destabilization of the airway of the subject, as identified by stability module 54, control module 56 begins to incrementally decrease the resistance of circuit valve 52, thereby incrementally increasing the flow of gas from circuit 44 to the airway of the subject, until the airway stabilizes. In one embodiment, if the resistance of the circuit valve 52 has been reduced and the airway of the subject stabilizes, control module incrementally increases the resistance of circuit valve 52, thereby incrementally decreasing the flow of gas from circuit 44 to the airway of the subject, until the flow is stopped or slowed significantly, or until another destabilization is identified by stability module 54.

In one embodiment, in addition to controlling the resistance of circuit valve 52, control module 56 controls an adjustable resistance of exhalation valve 28 based on determinations of the stability of the airway of the subject made by stability module 54. For example, control module 56 may control the resistance of exhalation valve 28 in the manner described above with respect to FIG. 4. In the embodiment illustrated in FIG. 6, control module 56 may coordinate control of exhalation valve 28 and circuit valve 52 to enhance one or more aspects of the therapy provided to the subject by system 40. By way of non-limiting example, control module 56 may increase the resistance of exhalation valve 28 and decrease the resistance of circuit valve 52 concomitantly to support the airway of the subject if stability module 54 identifies airway instability. As another example, control module 56 may implemented a stepped control scheme in which pressure in the airway of the subject is increased first by adjusting the resistance of one of the valves (e.g., increasing the resistance of exhalation valve 28) and then the resistance of the other valve (e.g., decreasing the resistance of circuit valve 52) until the airway of the subject stabilizes.

Settings module 58 is configured to enable the subject to configure, at least somewhat, the manner in which control module 56 responds to decreases in the stability of the airway. For example, settings module 58 may enable the subject to set a sensitivity of control module 56 to airway instability, an amount of increase to be applied to the resistance of exhalation valve 28 to exhaled gas in response to detected airway instability, an amount of decrease to be applied to the resistance of circuit valve 52 in response to detected airway instability, and/or configure other parameters of system 40 controlled by control module 56 (e.g., parameters of pressure generator 42, etc.). In one embodiment, settings module 58 is accessible to the subject via a user interface. The user interface may be carried on body 14, or may include a communication port through which the subject connects system 40 with another processing entity (e.g., a computer, a mobile phone, a personal digital assistant, etc.) for configuration of settings module 58.

Subject monitoring module 59 is configured to monitor the state of OSA or another condition suffered by the subject, and to provide results of this monitoring to a user via user interface 49. In one embodiment, subject monitoring module 59 operates in substantially the same manner as subject monitoring module 39. In one embodiment, information obtained and/or generated by subject monitoring module 39 is implemented by control module 56 to determine the manner in which control module 56 controls pressure generator 42 and/or circuit valve 52 in delivering gas to respiration appliance 10.

In one embodiment, processor 50 includes one or more modules that communicate with one or more therapeutic systems external to system 40. These modules may function to ensure that the aspects of therapy that are controlled by processor 50 are coordinated with therapy being provided to the subject by the one or more external systems. For example, the therapy provided by system 40 may be coordinated with one or more of insomnia therapy, pain control therapy, diagnostic devices and/or systems, light therapy, administration of medication, and/or other therapies and/or diagnostics that might be enhanced or impeded by the airway support and/or pressure provided by system 40.

Figure 7:
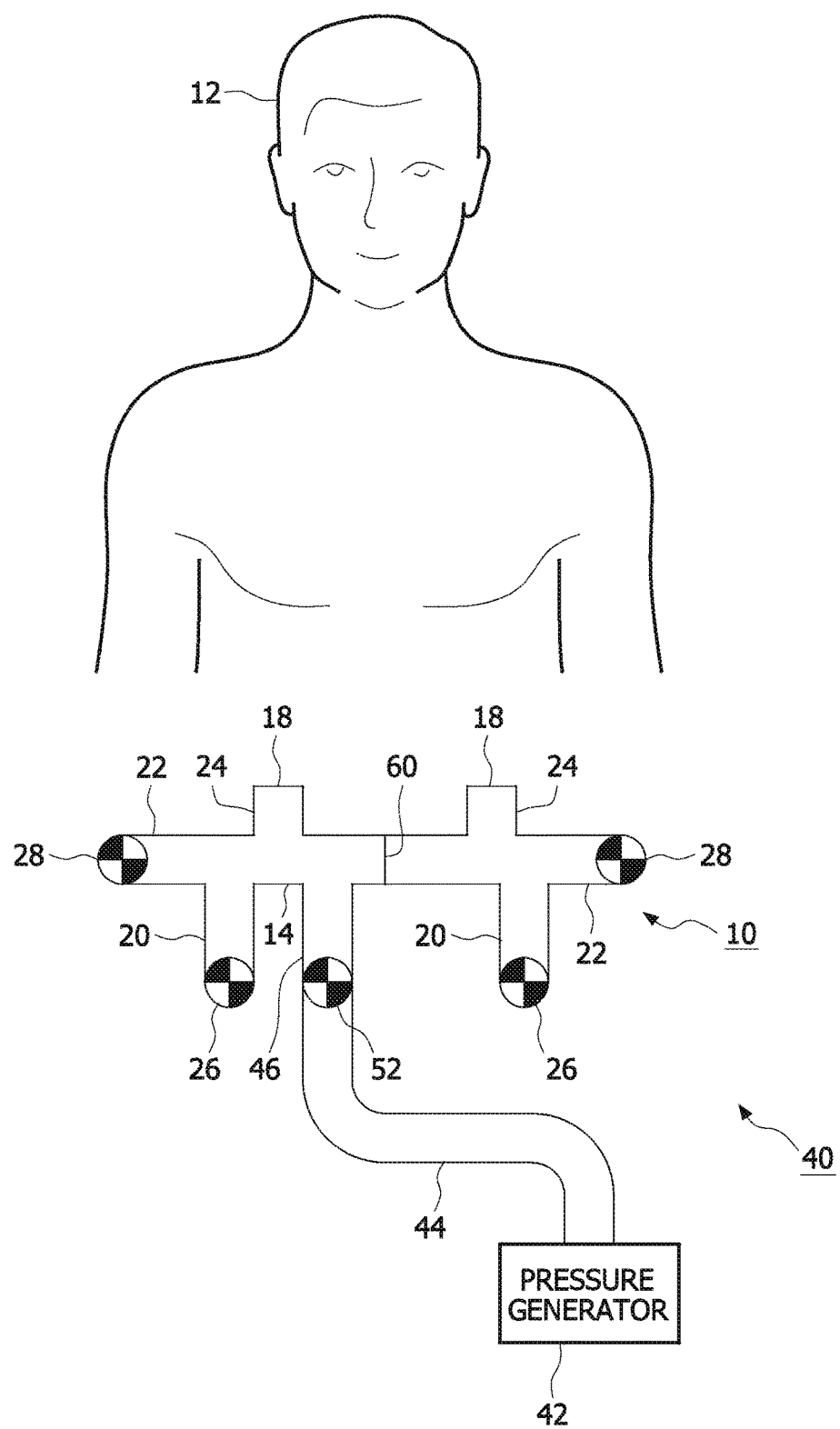
FIG. 7 illustrates a system configured to support the airway of a subject, in accordance with one or more embodiments of the invention.

FIG. 7 is a diagram of an embodiment of system 40 in which body 14 encloses the nostrils of subject 12, and in which the pressurized flow of breathable gas delivered from circuit 44 to body 14 is provided to only (or substantially only) one of the nostrils. In some instances, in addition to only providing the pressurized flow of breathable gas to one of the nostrils, respiration appliance 10 may be configured such that gas flows between one of the nostrils and ambient atmosphere with different resistances than gas flows between the other nostril and ambient atmosphere.

More particularly, body 14 is configured to form a single flow path from circuit port 52 to a single one of subject interface openings 18. In order to form this single flow path, body 14 may include one or more interior barriers 60 to gas flow that guides the flow of pressurized gas from circuit port 52 to the single one of subject interface openings 18 while blocking access of the flow of pressurized gas to the other subject interface opening. Although interior barrier 60 is illustrated in FIG. 7 as a single, impenetrable barrier, this is not intended to be limiting. In one embodiment a plurality of barrier members perform the functionality attributed to interior barrier 60 herein. In one embodiment, interior barrier 60 does not seal the flow of gas between the flow paths, but instead restricts access between the flow paths. In one embodiment interior barrier 60 includes a one-way valve that enables gas to flow in one direction between the flow paths formed within body 14.

In general, subject 12 may find the provision of the pressurized flow of breathable gas from circuit 44 into the airway of subject 12 to be obtrusive. By directing the pressurized flow of breathable gas from circuit 44 into a single one of the nostrils of subject 12, the obtrusiveness of the flow may be reduced while still providing the benefit of pressurizing the airway of subject 12. For example, by only providing the flow of gas from circuit 44 to one of the nostrils of subject 12, coldness and/or drying experienced by subject 12 in the nasal passages due to the flow of gas from circuit 44 may be reduced as exhalation and/or inhalation through the other nostril provides warmth and/or moisture to both of the nasal passages. As another example, the direction of the flow of gas from circuit 44 to only one of the nostrils of subject 12 may reduce the audible noise associated with breathing against air flow.

As can be seen in FIG. 7, in one embodiment, interior barrier 60 separates the flow paths that communicate gas between subject interface openings 18 and ambient atmosphere such that a first subset of flow paths formed within body 14 communicate gas between ambient atmosphere and one of subject interface openings 18 and a second subset of flow paths formed within body 14 communicate gas between ambient atmosphere and the other subject interface opening 18. The separation created by interior barrier 60 effectively seals the first subset of flow paths from the second subset of flow paths.

As was described above, circuit 44 is detachable from circuit port 46, and circuit port 46 can be closed (e.g., by circuit valve 52, by a stopper, etc.). If circuit 44 is detached and circuit port 46 is closed, then respiration appliance 10 provides support to the airway of subject 12 during exhalation by virtue of the resistances of the first subset of flow paths and the second set of flow paths to gas flow within body 14 from the nostrils of subject 12 to ambient atmosphere.

In one embodiment, the first subset of flow paths have the same cumulative resistances to gas flows from subject interface opening 18 to atmosphere and from atmosphere to subject interface opening 18 as the second subset of flow paths. In one embodiment, the first subset of flow paths have different cumulative resistances than the second subset of flow paths for gas flows from subject interface opening 18 to atmosphere and/or from atmosphere to subject interface opening 18.

For example, in one configuration, inhalation port 20 corresponding to the second subset of flow paths (i.e., the flow paths that do not receive the flow of gas from circuit 44) is blocked completely. In this configuration, the nostril in communication with the second subset of flow paths exhales gas out of body 14 through the corresponding exhalation port 22, but does not receive gas during inhalation. As a result, subject 12 is forced to inhale solely through the nostril that receives gas from the first subset of flow paths, which may enhance the support of the airway provided by the pressurized flow of breathable gas provided to the first subset of flow paths.

In one configuration, exhalation port 22 corresponding to the second subset of flow paths is blocked completely. In this configuration, the nostril in communication with the second subset of flow paths inhales gas from atmosphere through the corresponding inhalation port 20. However, during exhalation, only the nostril that receives the flow of gas from circuit 44 exhales gas to atmosphere through body 14 by way of the corresponding exhalation valve.

This active individual control of the resistances being applied to the left and right sides of the nose individually can be advantageous when considering nasal cycling. For example, a very low expiratory resistance could be set on the side which already has limited flow due to high intrinsic nasal resistance. The opposite side could have higher valve resistance during expiration. An algorithm estimating and tracking nasal resistance could be used to maximize comfort to the patient in this manner.

Figure 8:
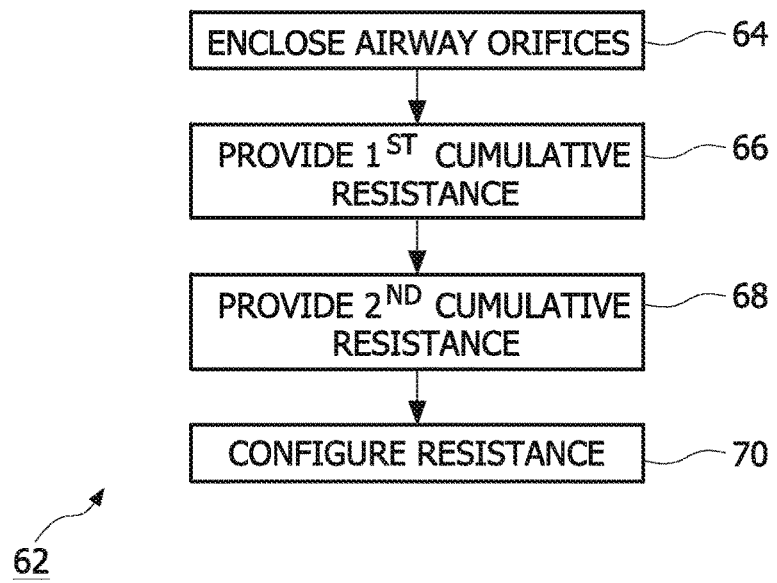
FIG. 8 illustrates a method of supporting the airway of a subject, in accordance with one or more embodiments of the invention.

FIG. 8 illustrates a method 62 of supporting the airway of a subject as the subject breathes. The operations of method 62 presented below are intended to be illustrative. In some embodiments, method 62 may be accomplished with one or more additional operations not described, and/or without one or more of the operations discussed. Additionally, the order in which the operations of method 62 are illustrated in FIG. 8 and described below is not intended to be limiting. Although the operations of method 62 are described below with references to components of a respiration appliance that is the same as or similar to respiration appliance 10 (shown in FIGS. 1-7 and described above), this is not intended to be limiting. Method 62 may be implemented in a variety of other contexts without departing from the scope of this disclosure.

At an operation 64, one or more external orifices of the airway of the subject are enclosed. The one or more external orifices of the airway of the subject may be enclosed with a body that forms a plurality of flow paths between the one or more external orifices of the airway and ambient atmosphere. The plurality of flow paths include a first subset of flow paths made up of one or more, but not all of, the plurality of flow paths. In one embodiment, the body is the same as or similar to body 14 (shown in FIGS. 1-7 and described above).

At an operation 66, during inhalation by the subject, a first cumulative resistance to gas flow within the plurality of flow paths for gas flow through the body from ambient atmosphere to the one or more external orifices of the airway is provided. The first cumulative resistance is low enough that is inhaled from ambient atmosphere into the one or more external orifices of the airway substantially unimpeded. In one embodiment, operation 66 is performed, at least in part, by one or more inhalation valves that are the same as or similar to inhalation valves 26 (shown in FIGS. 1-7 and described above).

At an operation 68, during exhalation by the subject, a second cumulative resistance to gas flow within the plurality of flow paths for gas flow through the body from the one or more external orifices of the airway to ambient atmosphere is provided. The second cumulative resistance to gas flow is provided limiting the flow of gas through the first subset of flow paths without limiting the flow of gas through the other flow paths in the plurality of flow paths formed by the body. The second cumulative resistance is high enough that the gas being exhaled through the body elevates pressure within the airway of the subject such that the elevated pressure supports the airway of the subject. In one embodiment, operation 68 is performed, at least in part by the inhalation valves. The other flow paths in the plurality of flow paths may include one or more exhalation valves that are the same as or similar to exhalation valves 28 (shown in FIGS. 1-7 and described above).

At an operation 70, the second cumulative resistance is adjusted. In one embodiment, the second cumulative resistance is adjusted by manipulating a control of the one or more exhalation valves and/or by replacing the one or more exhalation valves with valves of different resistances.

Figure 9:
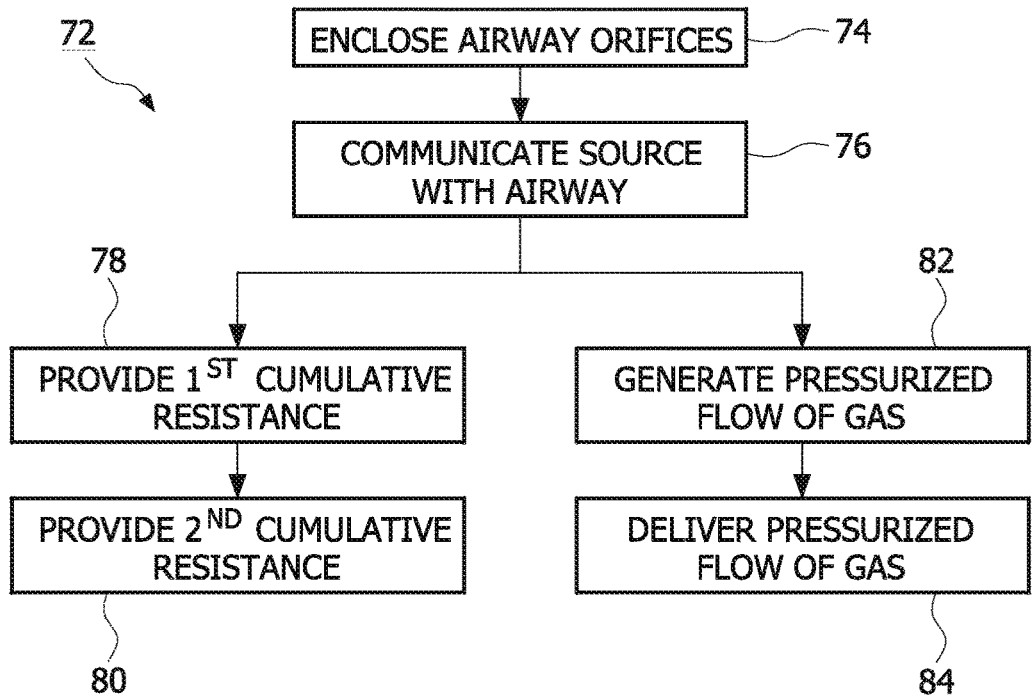
FIG. 9 illustrates a method of supporting the airway of a subject, in accordance with one or more embodiments of the invention.

FIG. 9 illustrates a method 72 of supporting the airway of a subject as the subject breathes. The operations of method 72 presented below are intended to be illustrative. In some embodiments, method 72 may be accomplished with one or more additional operations not described, and/or without one or more of the operations discussed. Additionally, the order in which the operations of method 72 are illustrated in FIG. 9 and described below is not intended to be limiting. Although the operations of method 72 are described below with references to components of a system that is the same as or similar to system 40 (shown in FIGS. 5-7 and described above), this is not intended to be limiting. Method 72 may be implemented in a variety of other contexts without departing from the scope of this disclosure.

At an operation 74, one or more external orifices of the airway of the subject are enclosed. The one or more external orifices of the airway of the subject may be enclosed with a body that forms a plurality of flow paths between the one or more external orifices of the airway and ambient atmosphere. The plurality of flow paths include a first subset of flow paths made up of one or more, but not all of, the plurality of flow paths. In one embodiment, the body is the same as or similar to body 14 (shown in FIGS. 5-7 and described above).

At an operation 76, a source of a pressurized flow of breathable gas is placed in fluid communication with the enclosed one or more external orifices of the airway of the subject. In one embodiment, the source of the pressurized flow of breathable gas is a pressure generator that is the same as or similar to pressure generator 42 (shown in FIGS. 5-7 and described above). In one embodiment, operation 76 is performed by a circuit and a circuit port that are the same as or similar to circuit 44 and circuit port 46 (shown in FIGS. 5-7 and described above).

At an operation 78, during inhalation by the subject, a first cumulative resistance to gas flow within the plurality of flow paths for gas flow through the body from ambient atmosphere to the one or more external orifices of the airway is provided. The first cumulative resistance is low enough that is inhaled from ambient atmosphere into the one or more external orifices of the airway substantially unimpeded. In one embodiment, operation 78 is performed, at least in part, by one or more inhalation valves that are the same as or similar to inhalation valves 26 (shown in FIGS. 1-7 and described above).

At an operation 80, during exhalation by the subject, a second cumulative resistance to gas flow within the plurality of flow paths for gas flow through the body from the one or more external orifices of the airway to ambient atmosphere is provided. The second cumulative resistance to gas flow is provided limiting the flow of gas through the first subset of flow paths without limiting the flow of gas through the other flow paths in the plurality of flow paths formed by the body. The second cumulative resistance is high enough that the gas being exhaled through the body elevates pressure within the airway of the subject such that the elevated pressure supports the airway of the subject. In one embodiment, operation 80 is performed, at least in part by the inhalation valves. The other flow paths in the plurality of flow paths may include one or more exhalation valves that are the same as or similar to exhalation valves 28 (shown in FIGS. 1-7 and described above).

At an operation 82, a pressurized flow of breathable gas is generated. In one embodiment, operation 82 is performed by the pressure generator.

At an operation 84, the pressurized flow of breathable gas is delivered to the one or more enclosed orifices of the airway of the subject. The delivery of the pressurized for of breathable gas to the one or more external orifices of the airway of the subject may include conveying the flow of breathable gas from the pressure generator, receiving the conveyed flow of breathable gas, and directing the flow of breathable gas to the one or more external orifices of the airway of the subject. In one embodiment, operation 84 is performed by a circuit and respiration appliance that are the same as or similar to circuit 44 and respiration appliance 10 (shown in FIGS. 5-7 and illustrated above).

In one embodiment, the enclosed one or more external orifices of the airway of the subject comprise the nostrils of the subject. In this embodiment, operation 84 may comprise directing the pressurized flow of breathable gas from the circuit to a single one of the nostrils of the subject while sealing the pressurized flow of breathable gas from reaching the other nostril of the subject. This portion of operation 84 may be performed by an interior barrier within the respiration appliance that is the same as or similar to interior barrier 60 (shown in FIG. 7 and described above).

Figure 10:
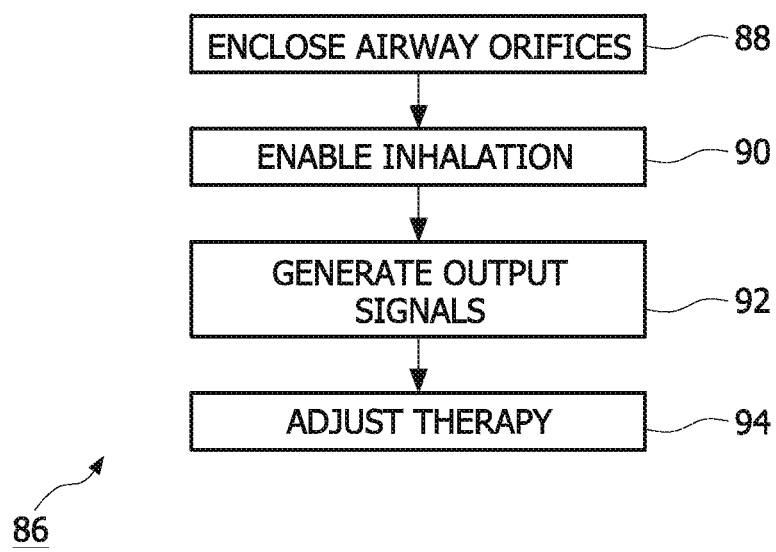
FIG. 10 illustrates a method of supporting the airway of a subject, in accordance with one or more embodiments of the invention.

FIG. 10 illustrates a method 86 of supporting the airway of a subject as the subject breathes. The operations of method 86 presented below are intended to be illustrative. In some embodiments, method 86 may be accomplished with one or more additional operations not described, and/or without one or more of the operations discussed. Additionally, the order in which the operations of method 86 are illustrated in FIG. 10 and described below is not intended to be limiting. Although the operations of method 86 are described below with references to components of a system that is the same as or similar to system 40 (shown in FIGS. 4 and 6 and described above), this is not intended to be limiting. Method 86 may be implemented in a variety of other contexts without departing from the scope of this disclosure.

At an operation 88, one or more external orifices of the airway of the subject are enclosed. The one or more external orifices of the airway of the subject may be enclosed with a body that forms a plurality of flow paths between the one or more external orifices of the airway and ambient atmosphere. The plurality of flow paths include a first subset of flow paths made up of one or more, but not all of, the plurality of flow paths. In one embodiment, the body is the same as or similar to body 14 (shown in FIGS. 4 and 6 and described above).

At an operation 90, gas in ambient atmosphere is enabled to reach the enclosed one or more external orifices with relatively little resistance such that the subject is able to inhale freely through the enclosed one or more external orifices. In one embodiment, operation 90 is performed by one or more inhalation valves that are the same as or similar to inhalation valves 26 (shown in FIGS. 4 and 6 and described above).

At an operation 92, one or more output signals are generated that convey information related to the stability of the airway of the subject. In one embodiment, operation 92 is performed by one or more sensors that are the same as or similar to sensors 30 (shown in FIGS. 4 and 6 and described above).

At an operation 94, one or more parameters of a therapy that supports the airway of the subject is adjusted based on the output signals generated at operation 92. The one or more parameters may include, for example, a resistance to gas flow of one or more flow paths through which gas is communicated from the enclosed one or more external orifices of the airway of the subject to ambient atmosphere. The one or more parameters may include, by way of non-limiting example, a parameter (e.g., flow rate, pressure, etc.) of a pressurized flow of gas provided to the one or more external orifices of the airway of the subject. In one embodiment, operation 94 is performed by a processor that is the same as or similar to processor 32 or processor 50 (shown in FIGS. 4 and 6 and described above) that controls one or more exhalation valves similar to or the same as exhalation valves 28 (shown in FIGS. 4 and 6 and described above), one or more circuit valves that are the same as or similar to circuit valve 52 (shown in FIG. 6 and described above), and/or a pressure generator that is the same as or similar to pressure generator 42 (shown in FIG. 6 and described above).

The systems and methods described above have been set forth as providing an elevated pressure within the airway of a subject for the purposes of airway support. This should not be viewed as limiting. The skilled artisan will appreciate that the systems and methods described herein may be implemented to elevate pressure within the airway for other therapeutic purposes as well. For example, controlling the pressure within the airway of the subject via a resistance differential between inhalation and exhalation may be implemented to detect and/or treat acute pulmonary edema by maximizing respiratory function, enlisting increased amounts of alveoli in breathing, reducing or retarding fluid build-up within the lungs, and/or providing other therapeutic benefits.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of supporting the airway of a subject as the subject breathes, the method comprising:
   during inhalation of a subject, providing a first resistance to gas flow for gas passing from ambient atmosphere into one or more external orifices of the airway of the subject;
   during exhalation of the subject, providing a second resistance to gas flow for gas passing from the one or more external orifices of the airway of the subject to ambient atmosphere, wherein the first resistance is lower than the second resistance such that during inhalation gas passes from ambient atmosphere into the one or more external orifices of the airway of the subject substantially unimpeded and during exhalation the second resistance elevates pressure within the airway of the subject such that the elevated pressure supports the airway of the subject;
   receiving a pressurized flow of breathable gas;
   directing the pressurized flow of breathable gas to the one or more external orifices of the airway of the subject as the subject breathes;
   generating one or more output signals that convey information related to the stability of the airway of the subject with one or more sensors; and
   adjusting a flow rate of the pressurized flow of breathable gas based on the information in the one or more output signals generated by the one or more sensors.

2. The method of claim 1, wherein the one or more sensors comprise a transducer configured to generate one or more output signals that convey information related to vibration in the airway of the subject.

3. The method of claim 1, wherein the information related to the stability of the airway of the subject comprise flow and/or pressure of gas at or near the airway of the subject.

4. A respiration appliance configured to support the airway of a subject as the subject breathes, the respiration appliance comprising:
   means for, during inhalation of a subject, providing a first resistance to gas flow for gas passing from ambient atmosphere into one or more external orifices of the airway of the subject;
   means for, during exhalation of the subject, providing a second resistance to gas flow for gas passing from the one or more external orifices of the airway of the subject to ambient atmosphere, wherein the first resistance is lower than the second resistance such that during inhalation gas passes from ambient atmosphere into the one or more external orifices of the airway of the subject substantially unimpeded and during exhalation the second resistance elevates pressure within the airway of the subject such that the elevated pressure supports the airway of the subject;
   means for receiving a pressurized flow of breathable gas;
   means for directing the pressurized flow of breathable gas to the one or more external orifices of the airway of the subject as the subject breathes;
   means for generating one or more output signals that convey information related to the stability of the airway of the subject; and
   means for adjusting a flow rate of the pressurized flow of breathable gas based on the information in the one or more output signals.

5. The respiration appliance of claim 4, wherein the means for generating comprise a transducer configured to generate one or more output signals that convey information related to vibration in the airway of the subject.

6. The respiration appliance of claim 4, wherein the information related to the stability of the airway of the subject comprise flow and/or pressure of gas at or near the airway of the subject.

7. A respiration appliance configured to support the airway of a subject as the subject breathes, the respiration appliance comprising:

means for, during inhalation of a subject, providing a first resistance to gas flow for gas passing from ambient atmosphere into one or more external orifices of the airway of the subject;

means for, during exhalation of the subject, providing a second resistance to gas flow for gas passing from the one or more external orifices of the airway of the subject to ambient atmosphere, wherein the first resistance is lower than the second resistance such that during inhalation gas passes from ambient atmosphere into the one or more external orifices of the airway of the subject substantially unimpeded and during exhalation the second resistance elevates pressure within the airway of the subject such that the elevated pressure supports the airway of the subject;

means for receiving a pressurized flow of breathable gas;

means for directing the pressurized flow of breathable gas to the one or more external orifices of the airway of the subject as the subject breathes; and means for adjusting a flow rate of the pressurized flow of breathable gas.

8. A respiration appliance configured to support the airway of a subject as the subject breathes, the respiration appliance comprising:

means for, during inhalation of a subject, providing a first resistance to gas flow for gas passing from ambient atmosphere into one or more external orifices of the airway of the subject;

means for, during exhalation of the subject, providing a second resistance to gas flow for gas passing from the one or more external orifices of the airway of the subject to ambient atmosphere, wherein the first resistance is lower than the second resistance such that during inhalation gas passes from ambient atmosphere into the one or more external orifices of the airway of the subject substantially unimpeded and during exhalation the second resistance elevates pressure within the airway of the subject such that the elevated pressure supports the airway of the subject;

means for receiving a pressurized flow of breathable gas; and means for directing the pressurized flow of breathable gas to the one or more external orifices of the airway of the subject as the subject breathes, wherein the one or more external orifices of the airway of the subject comprise the nostrils of the subject, and wherein the means for directing the pressurized flow of breathable gas to the one or more external orifices of the airway of the subject as the subject breathes comprises means for directing the pressurized flow of breathable gas from a circuit to a single one of the nostrils of the subject while sealing the pressurized flow of breathable gas from reaching the other nostril of the subject.

* * * * *